US007166312B2

(12) United States Patent
Christensen et al.

(10) Patent No.: US 7,166,312 B2
(45) Date of Patent: Jan. 23, 2007

(54) PROCESS FOR STABILIZING PROTEINS IN AN ACIDIC ENVIRONMENT WITH A HIGH-ESTER PECTIN

(75) Inventors: Tove Martel Ida Elsa Christensen, Allerod (DK); Jette Dina Kreiberg, Roskilde (DK); Hanne Thorsoe, Aarhus (DK); Hans Christian Buchholt, Brabrand (DK); Preben Rasmussen, Lyngby (DK); John Nielsen, Copenhagen (DK)

(73) Assignee: Danisco A/S, Copenhagen (DK)

( * ) Notice: Subject to any disclaimer, the term of this patent is extended or adjusted under 35 U.S.C. 154(b) by 402 days.

(21) Appl. No.: 10/165,528

(22) Filed: Jun. 7, 2002

(65) Prior Publication Data

US 2003/0157230 A1 Aug. 21, 2003

Related U.S. Application Data

(62) Division of application No. 08/983,364, filed as application No. PCT/EP96/03051 on Jul. 12, 1996, now abandoned.

(30) Foreign Application Priority Data

Jul. 14, 1995 (GB) .................................... 9514438

(51) Int. Cl.
*A23C 9/137* (2006.01)
(52) U.S. Cl. .................... 426/50; 426/40; 426/582; 426/583; 426/590; 426/654
(58) Field of Classification Search ............... 426/577, 426/49, 50, 52, 51, 34, 40, 582, 583, 590, 426/599, 654; 435/275
See application file for complete search history.

(56) References Cited

U.S. PATENT DOCUMENTS

| 4,200,694 | A | * | 4/1980 | Ishii et al. ................ 435/101 |
| 4,391,830 | A | * | 7/1983 | Gudnason et al. ............ 426/43 |
| 4,462,932 | A | | 7/1984 | Lonergan |
| 5,690,975 | A | * | 11/1997 | Akahoshi et al. ............. 426/34 |
| 6,083,540 | A | * | 7/2000 | Christensen et al. .......... 426/50 |
| 6,221,419 | B1 | * | 4/2001 | Gerrish ....................... 426/577 |
| 6,268,195 | B1 | | 7/2001 | Christensen et al. |

FOREIGN PATENT DOCUMENTS

| EP | 0664 300 A1 | 7/1995 |
| EP | 0709033 A1 | 10/1995 |
| GB | 1 221 874 | 2/1971 |
| JP | 8-112059 | 5/1996 |
| WO | WO 93/13212 | 7/1993 |
| WO | WO 94/25575 | 11/1994 |

OTHER PUBLICATIONS

Versteeg et al., *J. Food Sci.*, 45: 969-971, 998, 1980.*
Versteeg, et al., J. Food Sci., (1980) 45: 969-971, 998.
Khanh, et al., Characterization and expression of a genomic pectin methyl esterase-encoding gene in *Aspergillus niger*, Gene. 106 (1991) 71-77.
Glahn, et al., Copenhagen Pectin A/S Denmark; XP 000604284; Food Ingredients Europe Conference Proceedings 1994; The Netherlands; Casein-Pectin Interaction in sour Milk Beverages; pp. 252-256.
Hooydonk, et al., Nizo-nieuws: De bereiding van drinkyoghurt 2 De invloed van de produktsamenstelling; (date N.A.).
Abstract; Database WPI; Gelatin, et al., Section Ch, Week 9628; Derwent Publications Ltd., London, GB; An 96-271372; JP 08 112 059A; May 1996.
Richard, et al., XP 000615804; FEBS Letters 355 (1994); pp. 135-139; Molecular Cloning and Characterisation of a putative pectin methylesterase cDNA in *Arabidopsis thaliana* (L.).
Hall, et al.; XP 000815810; Plant Molecular Biology 25; pp 313-318; 1994; Molecular Characterisation of cDNA clones representing pecvtin esterase isozymes from tomato.
Kohn, et al., XP 000604261; Die Nahrung 29 (1985) 1, 75-85; Die Verteilung der freien und veresterten Carboxylgruppen im Pektinmolekud nach Einwirkung con Pektinesterase aus Aspergillus niger and Orangen.
R. Kohn, et al. Distribution of Free Carboxyl Groups in the Pectin Molecule After Treatment with Pectin Esterase, "Collection Czechoslov. Chem. Commun.," vol. 33, 1968, pp. 264-269.
Chambers English Dictionary, p. 356.
van Hooydonk el al, Voedingsmiddelen Technologie, 1992, vol. 15, No. 20, pp. 25-29.
Markovic et al, European Journal of Biochemistry, 1986, 158:455-462.
Swiss-Protein Accession ID 21KD_ DAUCA (1990).
FIA Japan; PEG/JK (dai-24a) Apr. 4, 1995 Glahn.
English Translation of FIA Japan, PEG/JK (dai-24a) Apr. 4, 1995 Glahn.
GENU New Products Development Seminar, Apr. 25, 1995, pp. 1-16.
Shokuhin Kogyo (Food Industry), Jul. 30, 1991, pp. 41-50.
J.J. Doeshurg, Pectic Substances in fresh and preserved fruits and vegetables, I.B.V.T.-Communication, 1965, No. 25, pp. 78-79.

* cited by examiner

*Primary Examiner*—Keith Hendricks
(74) *Attorney, Agent, or Firm*—Nixon & Vanderhye P.C.

(57) ABSTRACT

A process is described wherein there is added to an acidic environment, which contains at least one protein, a blockwise enzymatically de-esterified pectin, and wherein the pectin is a high ester pectin. Also described is a recombinant pectin methyl esterase.

27 Claims, 18 Drawing Sheets

Figure 1:
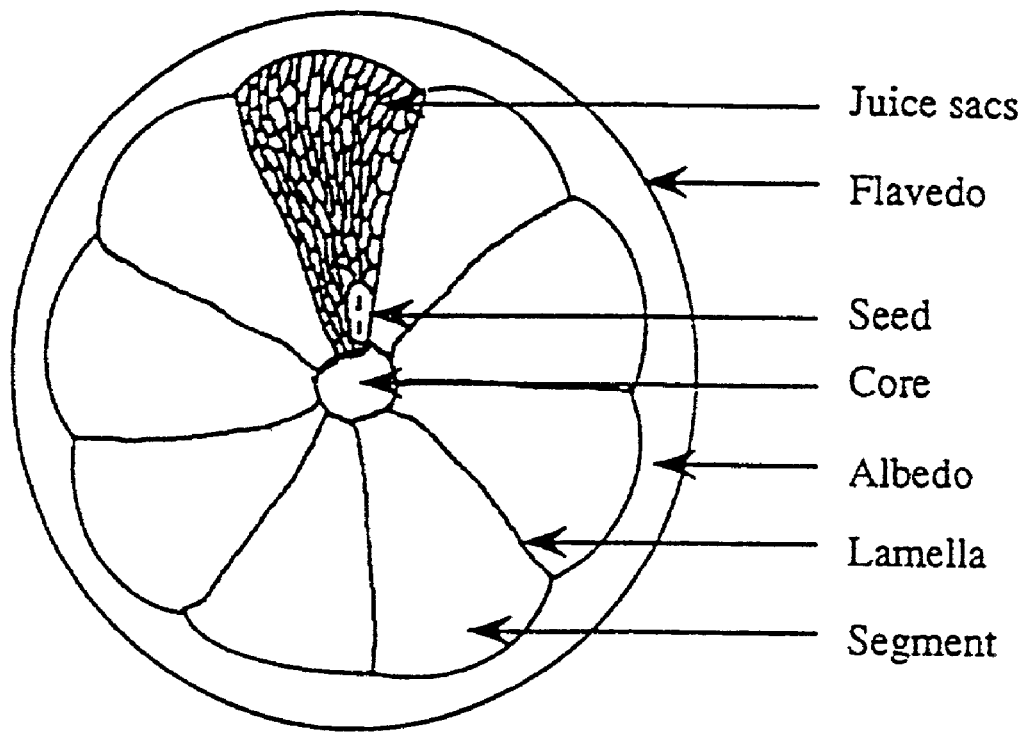

Figure 1. Schematic diagram of a citrus fruit

SEQUENCE LISTING

```
<160> NUMBER OF SEQ ID NOS: 56

<210> SEQ ID NO 1
<211> LENGTH: 362
<212> TYPE: PRT
<213> ORGANISM: Citrus navelina var. class 1

<400> SEQUENCE: 1

Met Ile Lys Asn Met Thr Asp Thr Asp Met Met Ile Met Arg Thr Ser
1               5                   10                  15

Asn Asn Arg Lys Leu Ile Glu Glu Thr Ser Thr Val Asp Gly Trp Pro
                20                  25                  30

Ala Trp Leu Ser Thr Gly Asp Arg Arg Leu Leu Gln Ser Ser Ser Val
            35                  40                  45

Thr Pro Asn Val Val Val Ala Asp Gly Ser Gly Asn Phe Lys Thr
    50                  55                  60

Val Ala Ala Ala Val Ala Ala Ala Pro Gln Gly Gly Thr Lys Arg Tyr
65                  70                  75                  80

Ile Ile Arg Ile Lys Ala Gly Val Tyr Arg Glu Asn Val Glu Val Thr
                85                  90                  95

Lys Lys His Lys Asn Ile Met Phe Ile Gly Asp Gly Arg Thr Arg Thr
                100                 105                 110

Ile Ile Thr Gly Ser Arg Asn Val Val Asp Gly Ser Thr Thr Phe Lys
            115                 120                 125

Ser Ala Thr Val Ala Val Val Gly Glu Gly Phe Leu Ala Arg Asp Ile
    130                 135                 140

Thr Phe Gln Asn Thr Ala Gly Pro Ser Lys His Gln Ala Val Ala Leu
145                 150                 155                 160

Arg Val Gly Ala Asp Leu Ser Ala Phe Tyr Asn Cys Asp Met Leu Ala
                165                 170                 175

Tyr Gln Asp Thr Leu Tyr Val His Ser Asn Arg Gln Phe Phe Val Asn
                180                 185                 190

Cys Leu Ile Ala Gly Thr Val Asp Phe Ile Phe Gly Asn Ala Ala Ala
            195                 200                 205

Val Leu Gln Asn Cys Asp Ile His Ala Arg Lys Pro Asn Ser Gly Gln
    210                 215                 220

Lys Asn Met Val Thr Ala Gln Gly Arg Ala Asp Pro Asn Gln Asn Thr
225                 230                 235                 240

Gly Ile Val Ile Gln Lys Ser Arg Ile Gly Ala Thr Ser Asp Leu Lys
                245                 250                 255

Pro Val Gln Gly Ser Phe Pro Thr Tyr Leu Gly Arg Pro Trp Lys Glu
                260                 265                 270

Tyr Ser Arg Thr Val Ile Met Gln Ser Ser Ile Thr Asp Val Ile His
            275                 280                 285
```

-continued

```
Pro Ala Gly Trp His Glu Trp Asp Gly Asn Phe Ala Leu Asn Thr Leu
        290                 295                 300

Phe Tyr Gly Glu His Gln Asn Ala Gly Ala Gly Thr Ser Gly
305                 310                 315                 320

Arg Val Lys Trp Lys Gly Phe Arg Val Ile Thr Ser Ala Thr Glu Ala
                325                 330                 335

Gln Ala Phe Thr Pro Gly Ser Phe Ile Ala Gly Ser Ser Trp Leu Gly
                340                 345                 350

Ser Thr Gly Phe Pro Phe Ser Leu Gly Leu
        355                 360

<210> SEQ ID NO 2
<211> LENGTH: 584
<212> TYPE: PRT
<213> ORGANISM: Citrus navelina var. class 1

<400> SEQUENCE: 2

Met Thr Arg Ile Lys Glu Phe Phe Thr Lys Leu Ser Glu Ser Ser Thr
  1               5                  10                  15

Asn Gln Asn Ile Ser Asn Ile Pro Lys Lys Lys Lys Leu Phe Leu
             20                  25                  30

Ala Leu Phe Ala Thr Leu Leu Val Val Ala Ala Val Ile Gly Ile Val
         35                  40                  45

Ala Gly Val Asn Ser Arg Lys Asn Ser Gly Asp Asn Gly Asn Glu Pro
 50                  55                  60

His His Ala Ile Leu Lys Ser Ser Cys Ser Ser Thr Arg Tyr Pro Asp
65                  70                  75                  80

Leu Cys Phe Ser Ala Ile Ala Ala Val Pro Glu Ala Ser Lys Lys Val
                 85                  90                  95

Thr Ser Gln Lys Asp Val Ile Glu Met Ser Leu Asn Ile Thr Thr Thr
            100                 105                 110

Ala Val Glu His Asn Tyr Phe Gly Ile Gln Lys Leu Leu Lys Arg Thr
        115                 120                 125

Asn Leu Thr Lys Arg Glu Lys Val Ala Leu His Asp Cys Leu Glu Thr
130                 135                 140

Ile Asp Glu Thr Leu Asp Glu Leu His Lys Ala Val Glu Asp Leu Glu
145                 150                 155                 160

Glu Tyr Pro Asn Lys Lys Ser Leu Ser Gln His Ala Asp Leu Lys
                165                 170                 175

Thr Leu Met Ser Ala Ala Met Thr Asn Gln Gly Thr Cys Leu Asp Gly
            180                 185                 190

Phe Ser His Asp Asp Ala Asn Lys His Val Arg Asp Ala Leu Ser Asp
        195                 200                 205

Gly Gln Val His Val Glu Lys Met Cys Ser Asn Ala Leu Ala Met Ile
    210                 215                 220

Lys Asn Met Thr Asp Thr Asp Met Met Ile Met Arg Thr Ser Asn Asn
225                 230                 235                 240

Arg Lys Leu Ile Glu Glu Thr Ser Thr Val Asp Gly Trp Pro Ala Trp
                245                 250                 255

Leu Ser Thr Gly Asp Arg Arg Leu Leu Gln Ser Ser Val Thr Pro
            260                 265                 270

Asn Val Val Val Ala Ala Asp Gly Ser Gly Asn Phe Lys Thr Val Ala
        275                 280                 285

Ala Ser Val Ala Ala Ala Pro Gln Gly Gly Thr Lys Arg Tyr Ile Ile
```

-continued

```
                  290                 295                 300
Arg Ile Lys Ala Gly Val Tyr Arg Glu Asn Val Glu Val Thr Lys Lys
305                 310                 315                 320

His Lys Asn Ile Met Phe Ile Gly Asp Gly Arg Thr Arg Thr Ile Ile
                325                 330                 335

Thr Gly Ser Arg Asn Val Val Asp Gly Ser Thr Thr Phe Lys Ser Ala
                340                 345                 350

Thr Val Ala Val Gly Glu Gly Phe Leu Ala Arg Asp Ile Thr Phe
                355                 360                 365

Gln Asn Thr Ala Gly Pro Ser Lys His Gln Ala Val Ala Leu Arg Val
370                 375                 380

Gly Ala Asp Leu Ser Ala Phe Tyr Asn Cys Asp Met Leu Ala Tyr Gln
385                 390                 395                 400

Asp Thr Leu Tyr Val His Ser Asn Arg Gln Phe Val Asn Cys Leu
                405                 410                 415

Ile Ala Gly Thr Val Asp Phe Ile Phe Gly Asn Ala Ala Val Leu
                420                 425                 430

Gln Asn Cys Asp Ile His Ala Arg Lys Pro Asn Ser Gly Gln Lys Asn
                435                 440                 445

Met Val Thr Ala Gln Gly Arg Ala Asp Pro Asn Gln Asn Thr Gly Ile
                450                 455                 460

Val Ile Gln Lys Ser Arg Ile Gly Ala Thr Ser Asp Leu Lys Pro Val
465                 470                 475                 480

Gln Gly Ser Phe Pro Thr Tyr Leu Gly Arg Pro Trp Lys Glu Tyr Ser
                485                 490                 495

Arg Thr Val Ile Met Gln Ser Ser Ile Thr Asp Val Ile His Pro Ala
                500                 505                 510

Gly Trp His Glu Trp Asp Gly Asn Phe Ala Leu Asn Thr Leu Phe Tyr
                515                 520                 525

Gly Glu His Gln Asn Ala Gly Ala Gly Ala Gly Thr Ser Gly Arg Val
                530                 535                 540

Lys Trp Lys Gly Phe Arg Val Ile Thr Ser Ala Thr Glu Ala Gln Ala
545                 550                 555                 560

Phe Thr Pro Gly Ser Phe Ile Ala Gly Ser Ser Trp Leu Gly Ser Thr
                565                 570                 575

Gly Phe Pro Phe Ser Leu Gly Leu
                580
```

<210> SEQ ID NO 3
<211> LENGTH: 1323
<212> TYPE: DNA
<213> ORGANISM: Citrus sinensis var. Navel

<400> SEQUENCE: 3

```
gtagcaatgc gcttgctatg atcaagaaca tgactgacac tgacatgatg atcatgagga      60
cttcaaacaa caggaagctg atagaggaga ccagtacggt tgatgggtgg ccggcgtggc     120
tgtccaccgg agacaggagg ctgttgcagt cctcgtcggt gacaccgaac gtggtggtgg     180
cagcagatgg cagcggaaac tttaagacgg tggcggcagc ggtggcggcg gctcctcagg     240
gaggcactaa gcggtatatt attaggatta aagccggtgt ttatcgggaa atgttgaggg     300
tgacaaagaa gcataaaaat ataatgttca tcggtgacgg gaggactaga actatcatca     360
caggaagtag aaatgtggtt gatggaagca caactttcaa gtctgctaca gttgctgttg     420
ttggtgaagg attcttggcc cgagacatta cattccaaaa cacagccggc ccctcaaagc     480
```

-continued

```
accaggcggt ggcactacga gtgggagctg acctttcagc attttacaat tgcgatatgt      540
tagcttacca agacacactc tacgtccact cgaaccgcca gttctttgtg aactgcttaa      600
ttgctggcac ggttgatttt attttggta acgctgcagc cgtgttacaa aattgtgaca       660
tccatgcacg aaagcccaat tccggccaaa aaatatggt cacagcccaa ggcagggctg       720
accctaacca aaacaccggc attgtcattc aaaaatctag gattggtgcc acctccgatt      780
taaaaccggt tcagggtagt ttcccgacgt acctcggcag gccctggaag gagtactcga      840
ggacggtgat catgcagtca tcgattactg acgtgatcca ccctgccggg tggcacgagt      900
gggatggtaa cttcgcgttg aacacattgt tttacggaga gcatcagaac gccggagccg      960
gtgccggaac ttcagggaga gtgaaatgga agggatttag ggttattaca agtgctaccg     1020
aggctcaagc ttttactcct ggaagcttca ttgctggtag tagctggctg ggctccactg     1080
gtttcccatt ctcccttggt ttgtaatatt cactaggagt tttaattaat atgttttgta     1140
ttagtggatc cataggtctc tggtctttca atttgtaata tttgattgag cgtgtcttat     1200
tcgtggcttc gatttcacaa atactattgt gtgattaaca agaaataaaa tagcatggga     1260
agaataataa tttccggctt ctttaaaaaa aaaaaaaaaa aaaaaaaaaa aaaaaaaaaa     1320
aaa                                                                   1323

<210> SEQ ID NO 4
<211> LENGTH: 1975
<212> TYPE: DNA
<213> ORGANISM: Citrus sinensis var. Navel

<400> SEQUENCE: 4
cttttgttct ctcttatcga gaaaaaaaat gacccgcata aaagaattct tcacaaaact       60
ttctgaatct tctaccaacc aaaacatttc caatattccc aagaaaaaaa agaaactatt      120
cttagctctt tttgcaacgc tactcgttgt cgctgccgta atcggcattg tcgccggagt      180
gaactcaaga aaaaactccg gcgacaacgg caacgagcct catcatgcta tcctcaaatc      240
atcatgtagc agcacaaggt acccggactt atgcttttcg gctattgctg ccgttccaga      300
ggcctccaaa aaggtgacaa gccaaaagga cgttattgag atgtccttaa acatcacaac      360
aacagccgtg gaacacaact acttcgggat tcagaagctc ttgagagaaa cgaatctcac      420
caaacgggaa aaggttgctc tccatgactg tcttgagacg atcgatgaga ctcttgatga      480
gttacacaaa gccgtcgagg atcttgagga gtacccgaac aagaaatctt tatcacagca      540
tgcggatgat ctcaaaaccc taatgagtgc cgcgatgacc aatcagggga cgtgtcttga      600
tgggttctct catgatgatg ctaataagca cgtgcgggat gcgttgtcag acggccaggt      660
tcatgttgag aagatgtgta gcaatgcgct tgctatgatc aagaacatga ctgacactga      720
catgatgatc atgaggactt caaacaacag gaagctgata gaggagacca gtacggttga      780
tgggtggccg gcgtggctgt ccaccggaga caggaggctg ttgcagtcct cgtcggtgac      840
accgaacgtg gtggtggcag cagatggcag cggaaacttt aagacggtgg cggcatcggt      900
ggcggcggct cctcagggag gcactaagcg gtatattatt aggattaaag ccggtgttta      960
tcggaaaaat gttgaggtga caagaagca taaaaatata atgttcatcg gtgacgggag     1020
gactagaact atcatcacag ggagtagaaa tgtggttgat ggaagcacaa cttttcaagtc    1080 tgctacagtt gctgttgttg gtgaaggatt cttggcccga gacattacat tccaaaacac     1140
agccggcccc tcaaagcacc aggcggtggc actacgagtg ggagctgacc tttcagcatt     1200
```

```
ttacaattgc gatatgttag cttaccaaga cacactctac gtccactcga accgccagtt    1260
ctttgtgaac tgcttaattg ctggcacggt tgattttatt tttggtaacg ctgcagccgt    1320
gttacaaaat tgtgacatcc atgcacgaaa gcccaattcc ggccaaaaaa atatggtcac    1380
agcccaaggc agggctgacc ctaaccaaaa caccggcatt gtcattcaaa aatctaggat    1440
tggtgccacc tccgatttaa aaccggttca gggtagtttc ccgacgtacc tcggcaggcc    1500
ctggaaggag tactcgagga cggtgatcat gcagtcatcg attactgacg tgatccaccc    1560
tgccgggtgg cacgagtggg atggtaactt cgcgttgaac acattgtttt acggagagca    1620
tcagaacgcc ggagccggtg ccggaacttc agggagagtt aaatgaagg gatttagggt    1680 tattacaagt gctaccgagg ctcaagcttt tactcctgga agcttcattg ctggtagtag    1740
ctggctgggc tccactggtt tcccattctc ccttggtttg taatattcac taggagtttt    1800
aattaatatg ttttgtatta gtggatccat aggtctctgg tctttcaatt tgtaatattt    1860
gattgagcgt gtcttattcg tggcttcgat ttcacaaata ctattgtgtg attaacaaga    1920
aataaaatag catgggaaga ataataattt ccggcttctt taaattaaaa aaaaa         1975
```

<210> SEQ ID NO 5
<211> LENGTH: 220
<212> TYPE: PRT
<213> ORGANISM: Citrus sinensis var. Navel

<400> SEQUENCE: 5

```
Ile Val Ala Gly Val Asn Ser Arg Lys Asn Ser Gly Asp Asn Gly Asn
 1               5                   10                  15

Glu Pro His His Ala Ile Leu Lys Ser Ser Cys Ser Ser Thr Arg Tyr
                20                  25                  30

Pro Asp Leu Cys Phe Ser Ala Ile Ala Ala Val Pro Glu Ala Ser Lys
            35                  40                  45

Lys Val Thr Ser Gln Lys Asp Val Ile Glu Met Ser Leu Asn Ile Thr
        50                  55                  60

Thr Thr Ala Val Glu His Asn Tyr Phe Gly Ile Gln Lys Leu Leu Lys
65                  70                  75                  80

Arg Thr Asn Leu Thr Lys Arg Glu Lys Val Ala Leu His Asp Cys Leu
                85                  90                  95

Glu Thr Ile Asp Glu Thr Leu Asp Glu Leu His Lys Ala Val Glu Asp
            100                 105                 110

Leu Glu Glu Tyr Pro Asn Lys Lys Ser Leu Ser Gln His Ala Asp Asp
        115                 120                 125

Leu Lys Thr Leu Met Ser Ala Ala Met Thr Asn Gln Gly Thr Cys Leu
    130                 135                 140

Asp Gly Phe Ser His Asp Ala Asn Lys His Val Arg Asp Ala Leu
145                 150                 155                 160

Ser Asp Gly Gln Val His Val Glu Lys Met Cys Ser Asn Ala Leu Ala
                165                 170                 175

Met Ile Lys Asn Met Thr Asp Thr Asp Met Met Ile Met Arg Thr Ser
            180                 185                 190

Asn Asn Arg Lys Leu Ile Glu Glu Thr Ser Thr Val Asp Gly Trp Pro
        195                 200                 205

Ala Trp Leu Ser Thr Gly Asp Arg Arg Leu Leu Gln
    210                 215                 220
```

<210> SEQ ID NO 6
<211> LENGTH: 660

-continued

```
<212> TYPE: DNA
<213> ORGANISM: Citrus sinensis var. Navel

<400> SEQUENCE: 6
attgtcgccg gagtgaactc aagaaaaaac tccggcgaca acggcaacga gcctcatcat      60
gctatcctca aatcatcatg tagcagcaca aggtacccgg acttatgctt ttcggctatt     120
gctgccgttc cagaggcctc caaaaaggtg acaagccaaa aggacgttat tgagatgtcc     180
ttaaacatca caacaacagc cgtggaacac aactacttcg ggattcagaa gctcttgaag     240
agaacgaatc tcaccaaacg ggaaaaggtt gctctccatg actgtcttga gacgatcgat     300
gagactcttg atgagttaca caaagccgtc gaggatcttg aggagtaccc gaacaagaaa     360
tctttatcac agcatgcgga tgatctcaaa accctaatga gtgccgcgat gaccaatcag     420
gggacgtgtc ttgatgggtt ctctcatgat gatgctaata agcacgtgcg ggatgcgttg     480
tcagacggcc aggttcatgt tgagaagatg tgtagcaatg cgcttgctat gatcaagaac     540
atgactgaca ctgacatgat gatcatgagg acttcaaaca acaggaagct gatagaggag     600
accagtacgg ttgatgggtg gccggcgtgg ctgtccaccg agacaggag gctgttgcag      660

<210> SEQ ID NO 7
<211> LENGTH: 14
<212> TYPE: PRT
<213> ORGANISM: Citrus sinensis var. Navel

<400> SEQUENCE: 7

Ser Ala Thr Val Ala Val Val Gly Glu Gly Phe Leu Ala Arg
 1               5                  10

<210> SEQ ID NO 8
<211> LENGTH: 4
<212> TYPE: PRT
<213> ORGANISM: Citrus sinensis var. Navel

<400> SEQUENCE: 8

Tyr Ile Ile Arg
 1

<210> SEQ ID NO 9
<211> LENGTH: 8
<212> TYPE: PRT
<213> ORGANISM: Citrus sinensis var. Navel

<400> SEQUENCE: 9

Asn Ile Met Phe Ile Gly Asp Gly
 1               5

<210> SEQ ID NO 10
<211> LENGTH: 21
<212> TYPE: PRT
<213> ORGANISM: Citrus sinensis var. Navel

<400> SEQUENCE: 10

Ile Gly Ala Thr Ser Asp Leu Lys Pro Val Gln Gly Ser Phe Pro Thr
 1               5                  10                  15

Tyr Leu Gly Arg Pro
            20

<210> SEQ ID NO 11
<211> LENGTH: 15
<212> TYPE: PRT
<213> ORGANISM: Citrus sinensis var. Navel
```

```
<400> SEQUENCE: 11

Xaa Ser Ala Thr Val Ala Val Val Gly Glu Gly Phe Leu Ala Arg
 1               5                  10                  15

<210> SEQ ID NO 12
<211> LENGTH: 11
<212> TYPE: PRT
<213> ORGANISM: Citrus sinensis var. Navel

<400> SEQUENCE: 12

Xaa Ala Tyr Pro Gly Gln Ile Thr Ser Asn Met
 1               5                  10

<210> SEQ ID NO 13
<211> LENGTH: 12
<212> TYPE: PRT
<213> ORGANISM: Citrus sinensis var. Navel

<400> SEQUENCE: 13

Asn Cys Asp Met Leu Ala Tyr Gln Asp Thr Leu Tyr
 1               5                  10

<210> SEQ ID NO 14
<211> LENGTH: 16
<212> TYPE: PRT
<213> ORGANISM: Citrus sinensis var. Navel

<400> SEQUENCE: 14

Val Ile Thr Ser Ala Thr Glu Ala Gln Ala Phe Thr Pro Gly Ser Phe
 1               5                  10                  15

<210> SEQ ID NO 15
<211> LENGTH: 28
<212> TYPE: PRT
<213> ORGANISM: Citrus sinensis var. Navel

<400> SEQUENCE: 15

Val Ile Thr Ser Ala Thr Glu Ala Gln Ala Phe Thr Pro Gly Ser Phe
 1               5                  10                  15

Ile Ala Gly Ser Ser Trp Leu Gly Ser Thr Gly Phe
            20                  25

<210> SEQ ID NO 16
<211> LENGTH: 13
<212> TYPE: PRT
<213> ORGANISM: Citrus sinensis var. Navel

<400> SEQUENCE: 16

Ile Ala Gly Ser Ser Trp Leu Gly Ser Thr Gly Phe Pro
 1               5                  10

<210> SEQ ID NO 17
<211> LENGTH: 19
<212> TYPE: PRT
<213> ORGANISM: Citrus sinensis var. Navel

<400> SEQUENCE: 17

Asn Met Val Thr Ala Gln Gly Arg Ala Asp Pro Asn Gln Asn Thr Gly
 1               5                  10                  15

Ile Val Ile

<210> SEQ ID NO 18
```

<211> LENGTH: 38
<212> TYPE: PRT
<213> ORGANISM: Citrus sinensis var. Navel

<400> SEQUENCE: 18

Xaa Arg Ile Gly Ala Thr Ser Asp Leu Lys Pro Val Gln Gly Ser Phe
 1               5                  10                  15

Pro Thr Tyr Leu Gly Arg Pro Trp Lys Glu Tyr Ser Arg Thr Val Ile
            20                  25                  30

Met Gln Ser Ser Ile Thr
        35

<210> SEQ ID NO 19
<211> LENGTH: 27
<212> TYPE: PRT
<213> ORGANISM: Citrus sinensis var. Navel

<400> SEQUENCE: 19

Xaa Xaa Ile Gly Ala Thr Ser Asp Leu Lys Pro Val Gln Gly Ser Phe
 1               5                  10                  15

Pro Thr Tyr Leu Gly Arg Pro Xaa Lys Glu Tyr
            20                  25

<210> SEQ ID NO 20
<211> LENGTH: 21
<212> TYPE: PRT
<213> ORGANISM: Citrus sinensis var. Navel

<400> SEQUENCE: 20

Ser Arg Ile Gly Ala Thr Ser Asp Leu Lys Pro Val Gln Gly Ser Phe
 1               5                  10                  15

Pro Thr Tyr Leu Gly
            20

<210> SEQ ID NO 21
<211> LENGTH: 21
<212> TYPE: PRT
<213> ORGANISM: Citrus sinensis var. Navel

<400> SEQUENCE: 21

Ser Val Ile Gly Ala Thr Ser Asp Leu Lys Pro Val Gln Gly Ser Phe
 1               5                  10                  15

Pro Thr Tyr Leu Gly
            20

<210> SEQ ID NO 22
<211> LENGTH: 21
<212> TYPE: PRT
<213> ORGANISM: Citrus sinensis var. Navel

<400> SEQUENCE: 22

Ser Arg Met Gly Ala Thr Ser Asp Leu Lys Pro Val Gln Gly Ser Phe
 1               5                  10                  15

Pro Thr Tyr Leu Gly
            20

<210> SEQ ID NO 23
<211> LENGTH: 21
<212> TYPE: PRT
<213> ORGANISM: Citrus sinensis var. Navel

<400> SEQUENCE: 23

```
Ser Arg Ile Gly Ala Val Ser Asp Leu Lys Pro Val Gln Gly Ser Phe
 1               5                  10                  15
Pro Val Tyr Leu Gly
             20

<210> SEQ ID NO 24
<211> LENGTH: 19
<212> TYPE: PRT
<213> ORGANISM: Citrus sinensis var. Navel

<400> SEQUENCE: 24

Ser Ser Ser Val Thr Pro Asn Val Val Ala Ala Asp Ser Ser Gly
 1               5                  10                  15
Asn Phe Lys

<210> SEQ ID NO 25
<211> LENGTH: 16
<212> TYPE: DNA
<213> ORGANISM: UNI (M13-20 primer)

<400> SEQUENCE: 25
gtaaacgacg gccagt                                                     16

<210> SEQ ID NO 26
<211> LENGTH: 19
<212> TYPE: DNA
<213> ORGANISM: Citrus sinensis var. Navel

<400> SEQUENCE: 26
ggaaacagct atgaccatg                                                  19

<210> SEQ ID NO 27
<211> LENGTH: 20
<212> TYPE: DNA
<213> ORGANISM: Citrus sinensis var. Navel

<400> SEQUENCE: 27
gacaacggca acgagcctca                                                 20

<210> SEQ ID NO 28
<211> LENGTH: 21
<212> TYPE: DNA
<213> ORGANISM: Citrus sinensis var. Navel

<400> SEQUENCE: 28
gcacttgtaa taccctaaa t                                                21

<210> SEQ ID NO 29
<211> LENGTH: 20
<212> TYPE: DNA
<213> ORGANISM: Citrus sinensis var. Navel

<400> SEQUENCE: 29
cagggtagtt tcccgacgta                                                 20

<210> SEQ ID NO 30
<211> LENGTH: 20
<212> TYPE: DNA
<213> ORGANISM: Citrus sinensis var. Navel

<400> SEQUENCE: 30
tacgtcggga aactaccctg                                                 20
```

```
<210> SEQ ID NO 31
<211> LENGTH: 41
<212> TYPE: DNA
<213> ORGANISM: Citrus sinensis var. Navel

<400> SEQUENCE: 31
ctcctggaag cttcattgct ggaagcttct tgaagagaac g        41

<210> SEQ ID NO 32
<211> LENGTH: 20
<212> TYPE: DNA
<213> ORGANISM: Citrus sinensis var. Navel

<400> SEQUENCE: 32
gaagcttctt gaagagaacg                                 20

<210> SEQ ID NO 33
<211> LENGTH: 23
<212> TYPE: DNA
<213> ORGANISM: Citrus sinensis var. Navel

<400> SEQUENCE: 33
cgttctcttc aagaagaagc ttc                             23

<210> SEQ ID NO 34
<211> LENGTH: 22
<212> TYPE: DNA
<213> ORGANISM: Citrus sinensis var. Navel

<400> SEQUENCE: 34
gaggatagca tgatgaggct cg                              22

<210> SEQ ID NO 35
<211> LENGTH: 22
<212> TYPE: DNA
<213> ORGANISM: Citrus sinensis var. Navel

<400> SEQUENCE: 35
gcagttcaca agaactggc gg                               22

<210> SEQ ID NO 36
<211> LENGTH: 22
<212> TYPE: DNA
<213> ORGANISM: Citrus sinensis var. Navel

<400> SEQUENCE: 36
cctcatgatc atcatgtcag tg                              22

<210> SEQ ID NO 37
<211> LENGTH: 21
<212> TYPE: DNA
<213> ORGANISM: Citrus sinensis var. Navel

<400> SEQUENCE: 37
gctcctcagg gaggcactaa g                               21

<210> SEQ ID NO 38
<211> LENGTH: 21
<212> TYPE: DNA
<213> ORGANISM: Citrus sinensis var. Navel

<400> SEQUENCE: 38
cagcaatgaa gcttccagga g                               21
```

```
<210> SEQ ID NO 39
<211> LENGTH: 21
<212> TYPE: DNA
<213> ORGANISM: Citrus sinensis var. Navel

<400> SEQUENCE: 39
cttagtgcct ccctgaggag c                                              21

<210> SEQ ID NO 40
<211> LENGTH: 18
<212> TYPE: DNA
<213> ORGANISM: Citrus sinensis var. Navel

<400> SEQUENCE: 40
gccaccgcct ggtgcttt                                                  18

<210> SEQ ID NO 41
<211> LENGTH: 18
<212> TYPE: DNA
<213> ORGANISM: Citrus sinensis var. Navel

<400> SEQUENCE: 41
aaagcaccag gcggtggc                                                  18

<210> SEQ ID NO 42
<211> LENGTH: 20
<212> TYPE: DNA
<213> ORGANISM: Citrus sinensis var. Navel

<400> SEQUENCE: 42
gcgggatgcg ttgtcagacg                                                20

<210> SEQ ID NO 43
<211> LENGTH: 20
<212> TYPE: DNA
<213> ORGANISM: Citrus sinensis var. Navel

<400> SEQUENCE: 43
gaggcactaa gcggtatatt                                                20

<210> SEQ ID NO 44
<211> LENGTH: 18
<212> TYPE: DNA
<213> ORGANISM: Citrus sinensis var. Navel

<400> SEQUENCE: 44
gcaactgtag cagacttg                                                  18

<210> SEQ ID NO 45
<211> LENGTH: 20
<212> TYPE: DNA
<213> ORGANISM: Citrus sinensis var. Navel

<400> SEQUENCE: 45
cactgacatg atgatcatga                                                20

<210> SEQ ID NO 46
<211> LENGTH: 20
<212> TYPE: DNA
<213> ORGANISM: Citrus sinensis var. Navel

<400> SEQUENCE: 46
```

-continued

```
caattaagca gttcacaaag                                              20

<210> SEQ ID NO 47
<211> LENGTH: 20
<212> TYPE: DNA
<213> ORGANISM: Citrus sinensis var. Navel

<400> SEQUENCE: 47
aatataccgc ttagtgcctc                                              20

<210> SEQ ID NO 48
<211> LENGTH: 7
<212> TYPE: PRT
<213> ORGANISM: Citrus sinensis var. Navel

<400> SEQUENCE: 48

Met Leu Ala Tyr Gln Asp Thr
 1               5

<210> SEQ ID NO 49
<211> LENGTH: 20
<212> TYPE: DNA
<213> ORGANISM: Citrus sinensis var. Navel

<400> SEQUENCE: 49
atgytngcnt aycadgayac                                              20

<210> SEQ ID NO 50
<211> LENGTH: 7
<212> TYPE: PRT
<213> ORGANISM: Citrus sinensis var. Navel

<400> SEQUENCE: 50

Glu Ala Gln Ala Phe Thr Pro
 1               5

<210> SEQ ID NO 51
<211> LENGTH: 17
<212> TYPE: DNA
<213> ORGANISM: Citrus sinensis var. Navel
<220> FEATURE:
<223> OTHER INFORMATION: Primer to PME

<400> SEQUENCE: 51
gtraangcyt gngcytc                                                 17

<210> SEQ ID NO 52
<211> LENGTH: 6
<212> TYPE: PRT
<213> ORGANISM: Citrus sinensis var. Navel

<400> SEQUENCE: 52

Ser Ser Ser Val Thr Pro
 1               5

<210> SEQ ID NO 53
<211> LENGTH: 24
<212> TYPE: DNA
<213> ORGANISM: Citrus sinensis var. Navel

<400> SEQUENCE: 53
gaattcattg tcgccggagt gaac                                         24

<210> SEQ ID NO 54
```

```
-continued
<211> LENGTH: 24
<212> TYPE: DNA
<213> ORGANISM: Citrus sinensis var. Navel

<400> SEQUENCE: 54
aagaccagag acctatggat ccac                                        24

<210> SEQ ID NO 55
<211> LENGTH: 24
<212> TYPE: DNA
<213> ORGANISM: Citrus sinensis var. Navel

<400> SEQUENCE: 55
gaattctcct cgtcggtgac accg                                        24

<210> SEQ ID NO 56
<211> LENGTH: 24
<212> TYPE: DNA
<213> ORGANISM: Citrus sinensis var. Navel

<400> SEQUENCE: 56
aagaccagag acctatggat ccac                                        24
```

PROCESS FOR STABILIZING PROTEINS IN AN ACIDIC ENVIRONMENT WITH A HIGH-ESTER PECTIN

CROSS-REFERENCE TO RELATED APPLICATIONS

The application is a divisional of U.S. patent application Ser. No. 08/983,364, filed May 18, 1998, now abandoned which is the National Phase application under 35 U.S.C. § 371 of International Application PCT/EP96/03051, filed Jul. 12, 1996 and published in English, which claims priority to GB 9514438.2, filed Jul. 14, 1995.

The present invention relates to a process and an enzyme for use in such a process.

In particular, the present invention relates to a process for preparing and using an enzymatically modified pectin.

Pectin is an important commodity in today's industry. For example, it can be used in the food industry as a thickening or gelling agent, such as in the preparation of jams.

Pectin is a structural polysaccharide commonly found in the form of protopectin in plant cell walls. The backbone of pectin comprises α-1-4 linked galacturonic acid residues which are interrupted with a small number of 1,2 linked α-L-rhamnose units. In addition, pectin comprises highly branched regions with an almost alternating rhamno-galacturonan chain. These highly branched regions also contain other sugar units (such as D-galactose, L-arabinose and xylose) attached by glycosidic linkages to the C3 or C4 atoms of the rhamnose units or the C2 or C3 atoms of the galacturonic acid units. The long chains of α-1 linked galacturonic acid residues are commonly referred to as "smooth" regions, whereas the highly branched regions are commonly referred to as the "hairy regions".

Some of the carboxyl groups of the galacturonic residues are esterified (e.g. the carboxyl groups are methylated). Typically esterification of the carboxyl groups occurs after polymerisation of the galacturonic acid residues. However, it is extremely rare for all of the carboxyl groups to be esterified (e.g. methylated). Usually, the degree of esterification will vary from 0–90%. If 50% or more of the carboxyl groups are esterified then the resultant pectin is referred to as a "high ester pectin" ("HE pectin" for short) or a "high methoxyl pectin". If less than 50% of the carboxyl groups are esterified then the resultant pectin is referred to as a "low ester pectin" ("LE pectin" for short) or a "low methoxyl pectin". If the pectin does not contain any—or only a few—esterified groups it is usually referred to as pectic acid.

The structure of the pectin, in particular the degree of esterification (e.g. methylation), dictates many of the resultant physical and/or chemical properties of the pectin. For example, pectin gelation depends on the chemical nature of the pectin, especially the degree of esterification. In addition, however, pectin gelation also depends on the soluble-solids content, the pH and calcium ion concentration. With respect to the latter, it is believed that the calcium ions form complexes with free carboxyl groups, particularly those on a LE pectin.

Pectic enzymes are classified according to their mode of attack on the galacturonan part of the pectin molecule. A review of some pectic enzymes has been prepared by Pilnik and Voragen (Food Enzymology, Ed.: P. F. Fox: Elsevier; (1991); pp: 303–337). In particular, pectin methylesterases (EC 3.1.1.11), otherwise referred to as PMEs, de-esterify HE pectins to LE pectins or pectic acids. In contrast, and by way of example, pectin depolymerases split the glycosidic linkages between galacturonosyl methylester residues.

In more detail, PME activity produces free carboxyl groups and free methanol. The increase in free carboxyl groups can be easily monitored by automatic titration. In this regard, earlier studies have shown that some PMEs de-esterify pectins in a random manner, in the sense that they de-esterify any of the esterified (e.g. methylated) galacturonic acid residues on more than one of the pectin chains. Examples of PMEs that randomly de-esterify pectins may be obtained from fungal sources such as *Aspergillus aculeatus* (see WO 94/25575) and *Aspergillus japonicus* (Ishii et al J Food Sci 44 pp 611–14). Baron et al (Lebensm. Wiss. M-Technol 13 pp 330–333) apparently have isolated a fungal PME from *Aspergillus niger*. This fungal PME is reported to have a molecular weight of 39000 D, an isoelectric point of 3.9, an optimum pH of 4.5 and a $K_m$ value (mg/ml) of 3.

In contrast, some PMEs are known to de-esterify pectins in a block-wise manner, in the sense that it is believed they attack pectins either at non-reducing ends or next to free carboxyl groups and then proceed along the pectin molecules by a single-chain mechanism, thereby creating blocks of unesterified galacturonic acid units which are very calcium sensitive. Examples of such enzymes that block-wise enzymatically de-esterify pectin are plant PMEs. Up to 12 isoforms of PME have been suggested to exist in citrus (Pilnik W. and Voragen A. G. J. (Food Enzymology (Ed.: P. F. Fox); Elsevier; (1991); pp: 303–337). These isoforms have different properties.

Versteeg et al (J Food Sci 45 pp 969–971) apparently have isolated a PME from orange. This plant PME is reported to occur in multiple isoforms of differing properties. Isoform I has a molecular weight of 36000 D, an isoelectric point of 10.0, an optimum pH of 7.6 and a $K_m$ value (mg/ml) of 0.083. Isoform II has a molecular weight of 36200 D, an isoelectric point of 11.0, an optimum pH of 8.8 and a $K_m$ value (mg/ml) of 0.0046. Isoform m (HMW-PE) has a molecular weight of 54000 D, an isoelectric point of 10.2, an optimum pH of 8 and a $K_m$ value (mg/ml) of 0.041. However, to date there has been very limited sequence data for such PMEs.

According to Pilnik and Voragen (ibid), PMEs may be found in a number of other higher plants, such as apple, apricot, avocado, banana, berries, lime, grapefruit, mandarin, cherries, currants, grapes, mango, papaya, passion fruit, peach, pear, plums, beans, carrots, cauliflower, cucumber, leek, onions, pea, potato, radish and tomato. However, likewise, to date there has been very limited sequence data for such PMES.

Random or blockwise distribution of free carboxyl groups can be distinguished by high performance ion exchange chromatography (Schols et al Food Hydrocolloids 1989 6 pp 115–121). These tests are often used to check for undesirable, residual PME activity in citrus juices after pasteurisation because residual PME can cause, what is called. "cloud loss" in orange juice in addition to a build up of methanol in the juice.

PMEs have important uses in industry. For example, they can be used in or as sequestering agents for calcium ions. In this regard, and according to Pilnik and Voragen (ibid). cattle feed can be prepared by adding a slurry of calcium hydroxide to citrus peels after juice extraction. After the addition, the high pH and the calcium ions activate any native PME in the peel causing rapid de-esterification of the pectin and calcium pectate coagulation occurs. Bound liquid phase is released and is easily pressed out so that only a fraction of the original water content needs to be removed by expensive thermal drying. The press liquor is then used as animal feed.

Pilnik and Voragen (ibid) list uses of endogenous PMEs which include their addition to fruit juices to reduce the viscosity of the juice if it contains too much pectin derived from the fruit, their addition as pectinase solutions to the gas bubbles in the albedo of citrus fruit that has been heated to a core temperature of 20 to 40° C. in order to facilitate removal of peel and other membrane from intact juice segments (U.S. Pat. No. 4,284,651), and their use in protecting and improving the texture and firmness of several processed fruits and vegetables such as apple (Wiley & Lee 1970 Food Technol 24 1168–70), canned tomatoes (Hsu et al 1965 J Food Sci 30 pp 583–588) and potatoes (Bartolome & Hoff 1972 J Agric Food Chem 20 pp 262–266).

Glahn and Rolin (1994 Food Ingredients Europe, Conf Proceedings pp 252–256) report on the hypothetical application of the industrial "GENU pectin type YM-100" for interacting with sour milk beverages. No details are presented at all on how GENU pectin type YM-100 is prepared.

EP-A-0664300 discloses a chemical fractionation method for preparing calcium sensitive pectin. This calcium sensitive pectin is said to be advantageous for the food industry.

Thus, pectins and de-esterified pectins, in addition to PMEs, have an industrial importance. However, there is a continuing need to improve the known methods of stabilising proteins in an acidic environment but without adversely affecting the viscosity of that environment. In this regard, an adverse effect on the viscosity of the environment can compromise the overall appearance and/or texture and/or palatability and/or mouth feel of the resultant product.

According to a first aspect of the present invention there is provided a process comprising adding to an acidic environment, which contains at least one protein, a block-wise enzymatically de-esterified pectin, wherein the pectin is a high ester pectin.

According to a second aspect of the present invention there is provided a method of block-wise enzymatically de-esterifying a pectin comprising treating the pectin with a recombinant enzyme comprising any one of the amino acid sequences shown as SEQ. I.D. No.1 or SEQ. I.D. No. 2, or a variant, derivative or homologue thereof, including combinations thereof.

According to a third aspect of the present invention there is provided a recombinant enzyme comprising any one of the amino acid sequences shown as SEQ. I.D. No.1 or SEQ. I.D. No. 2. or a variant, derivative or homologue thereof, including combinations thereof.

According to a fourth aspect of the present invention there is provided a nucleotide sequence coding for the recombinant enzyme according to the present invention, wherein the nucleotide sequence comprises any one of the sequences shown as SEQ. I.D. No. 3 or SEQ. I.D. No. 4, or a variant, derivative or homologue thereof.

According to a fifth aspect of the present invention there is provided a nucleotide sequence coding for the recombinant enzyme according to the present invention wherein the nucleotide sequence is obtainable from NCIMB 40749 or NCIMB 40750, or a variant, derivative or homologue thereof.

According to a sixth aspect of the present invention there is provided a construct expressing or comprising the recombinant enzyme according to the present invention or a nucleotide sequence according to the present invention.

According to a seventh aspect of the present invention there is provided a vector expressing or comprising a construct according to the present invention or the recombinant enzyme according to the present invention or a nucleotide sequence according to the present invention.

According to an eighth aspect of the present invention there is provided a combination of constructs comprising at least a first construct expressing or comprising the recombinant enzyme according to the present invention or a nucleotide sequence according to the present invention; and a second construct comprising a gene of interest (GOI) and a promoter.

According to a ninth aspect of the present invention there is provided a cell, tissue or organ expressing or comprising a vector according to the present invention or a construct according to the present invention or the recombinant enzyme according to the present invention or a nucleotide sequence according to the present invention or a combination of constructs according to the present invention.

According to a tenth aspect of the present invention there is provided a transgenic organism expressing or comprising any of the afore-mentioned aspects of the present invention.

According to an eleventh aspect of the present invention there is provided NCIMB 40749 or NCIMB 40750.

According to a twelfth aspect of the present invention there is provided a recombinant PME enzyme which is immunologically reactive with an antibody raised against a purified recombinant enzyme according to the third aspect of the present invention, but not a tomato PME enzyme.

According to a thirteenth aspect of the present invention there is provided the use of the recombinant enzyme according to the present invention to reduce the number of ester groups of a pectin.

According to a fourteenth aspect of the present invention there is provided the use of the recombinant enzyme according to the present invention to de-esterify pectin in a block-wise manner.

According to a fifteenth aspect of the present invention there is provided the use of the recombinant enzyme according to the present invention to affect the calcium sensitivity of pectin.

According to a sixteenth aspect of the present invention there is provided the use of the recombinant enzyme according to the present invention to esterify pectin containing free carboxyl groups.

According to a seventeenth aspect of the present invention there is provided a pectin obtained by use of the recombinant enzyme according to the present invention, such as by the method according to the present invention.

According to an eighteenth aspect of the present invention there is provided a combination of enzymes comprising a recombinant enzyme according to the present invention and a fungal PME and/or an other pectin degrading enzyme (e.g. pectin lyase).

Other aspects of the present invention include the use of a pectin according to the present invention to prepare a foodstuff; and the use of a pectin according to the present invention to stabilise a protein in an acidic environment without adversely affecting the viscosity of the environment; and a recombinant nucleotide sequence coding for the enzyme according to the present invention.

Thus, the present invention relates to a new use of de-esterified pectins. The present invention also relates to a new recombinant PME to prepare such pectins.

Some of the key advantages of the present invention are that the de-esterified pectin of the present invention offers stability to proteins in an acidic environment without adversely affecting the viscosity of the environment.

A preferred embodiment of the first aspect of the present invention is a process comprising adding to an acidic environment, which contains at least one protein, a blockwise enzymatically de-esterified pectin prepared by use of recombinant DNA techniques, wherein the pectin is a high ester pectin.

The term "a block-wise enzymatically de-esterified pectin prepared by use of recombinant DNA techniques" means a pectin containing block-wise de-esterified groups wherein the pectin is prepared by treating (e.g. contacting) a pectin containing esterified groups with an enzyme that has been prepared by use of recombinant DNA techniques.

Some of the key advantages of this preferred aspect of the present invention are that the de-esterified pectin can be prepared with ease and with a relative degree of consistency. In this regard, the recombinant PME itself can be prepared fairly simply and easily and, also, to a high degree of homogeneity. This in turn, and unlike the prior art PME preparations, means that the resultant PME activity is more consistent and homogeneous so enables the overall de-esterification process to be more controlled.

The use of a block-wise enzymatically de-esterified pectin—which is preferably prepared by use of recombinant DNA techniques—in the process of the present invention for stabilising at least one protein in an acidic environment is of benefit as it allows proteins such as whey and milk proteins (such as casein) to be stable in acidic solutions. This is of importance for the drinks market, such as skimmed milk, fruit juices and whey protein drinks, wherein before it was only possible to retain the flavour of the key proteins under fairly high acidic conditions—such as pH 4.2—if high amounts of stabiliser were present.

We have now found that for some applications small amounts of the de-esterified pectin according to the present invention can be employed. At these low levels, the de-esterified pectin according to the present invention not only acts as a stabiliser but also it does not have an adverse effect on the final product.

If desired, the use of the de-esterified pectin of the present invention would enable food manufacturers to increase the pH bf foods, such as drinks. In this regard, in some cases the less acidic nature of the drinks may make them more palatable for people, especially infants. Thus, in contrast to the prior art processes, it is now possible to retain the flavour of those proteins at pH conditions higher than 4.2, such as up to pH 5.5 (such as pH 5.2) by use of the block-wise enzymatically de-esterified pectin, particularly the block-wise enzymatically de-esterified pectin prepared by use of recombinant DNA techniques.

In addition, it is believed that even under low pH conditions, such as pH 4.2 or less, the block-wise enzymatically de-esterified pectin—particularly the block-wise enzymatically de-esterified pectin prepared by use of recombinant DNA techniques—stabilises the protein(s) more than the prior art stabilisers that are used for those pH conditions.

A further advantage is that the recombinant PME is capable of producing a substantially homogeneous block-wise de-esterified pectin. By this we mean that substantially all of the pectin chains comprise at least two adjacent de-esterified carboxyl groups. However, for some applications it may not be necessary to prepare or use such a substantially homogeneous block-wise de-esterified pectin.

Without wishing to be bound by theory it is believed that the block-wise enzymatically de-esterified pectin—particularly that prepared by use of recombinant DNA techniques—stabilises the protein(s) by surrounding the protein(s) in a blanket of negative charges, thus forming a stable emulsion.

The recombinant PME enzyme of the present invention is useful for blockwise de-esterifying pectins when the pectins are contacted with the recombinant enzyme in a substantially aqueous medium. In some instances, de-esterifying pectins can increase the calcium ion sensitivity of a pectin—which in turn may be advantageous.

Alternatively, the recombinant PME enzyme of the present invention is useful for esterifying pectins when the pectins are contacted with the recombinant enzyme in a substantially non-aqueous medium, such as in the presence of methanol or in the presence of high concentrations of ammonium sulphate. This aspect is advantageous if, for example, it is desirable to reduce the calcium sensitivity of a pectin.

This method of esterifying pectins is advantageous because it obviates the need for the high temperature and methanol esterification conditions associated with the prior art processes. Thus, the present invention also includes the use of that esterified pectin in the preparation of a foodstuff, as well as the pectin per se.

In accordance with the present invention, the de-esterified pectin of the present invention is advantageous for the preparation of a foodstuff.

Typical foodstuffs include dairy products, meat products, poultry products, fish products and bakery products. Preferably, the foodstuff is a beverage.

The de-esterified pectin of the present invention is also advantageous for use as a stabiliser and/or viscosity modifier in the preparation of pharmaceuticals, pharmaceutical appliances, cosmetics and cosmetic appliances.

Preferably the acidic environment is an aqueous solution.

Preferably the aqueous solution is a beverage.

Preferably the beverage is a drinking yoghurt, a fruit juice or a beverage comprising whey protein.

Preferably the protein is derived or derivable from dairy products, such as milk or cheese.

Preferably the protein is casein or whey protein.

Preferably the acidic environment has a pH of from about 3.5 to about 5.5.

Preferably the acidic environment has a pH of from 4 to about 5.5.

Preferably, wherein the acidic environment has a pH of about 4.

Preferably the block-wise enzymatically de-esterified pectin, particularly that prepared by recombinant DNA techniques, is a high ester pectin containing about 80% ester groups or less (i.e. a degree of esterification (DE) of 80% or less), preferably about 75% ester groups or less (i.e. a DE of about 75% or less). In this regard, the ratio of free carboxyl groups to esterified carboxyl groups on the pectin is from 1:1 to 1:4, preferably from 1:2 to 1:3.

Preferably, the block-wise enzymatically de-esterified pectin contains about 76% ester groups.

In some instances, preferably the block-wise enzymatically de-esterified pectin is sensitive to $Ca^{2+}$ ions. Calcium sensitivity can be determined by following the Protocol as mentioned in the Examples.

More preferably, however, the block-wise enzymatically de-esterified pectin, particularly that prepared by recombinant DNA techniques, is insensitive to $Ca^{2+}$ ions. Calcium insensitivity can be determined by following the Protocol as mentioned in the Examples.

Preferably the block-wise enzymatically de-esterified pectin has a high molecular weight.

Typically, the molecular weight is between from about 50 KD to about 150 KD.

Preferably the block-wise enzymatically de-esterified pectin is prepared by treating a pectin with a recombinant pectin methyl esterase that de-esterifies two or more adjacent galacturonic acid residues of the pectin on at least substantially all of the pectin chains.

Preferably the recombinant pectin methyl esterase is derived from a PME obtainable from a plant.

The term "derived from a PME obtainable from a plant" means that the recombinant PME has a sequence similar to that of a PME that is obtainable from a plant, providing the recombinant PME can de-esterify pectin in a block-wise manner.

Preferably the plant is a fruit.

Preferably the fruit is a citrus fruit.

Preferably the citrus fruit is an orange.

Preferably the recombinant pectin methyl esterase is derived from a PME obtainable from the lamella or albedo of an orange. For reference, a cross-section of a typical citrus fruit is shown in FIG. 1 where the lamella and albedo are indicated. The term "derived from a PME obtainable from the lamella or albedo of an orange" means that the recombinant PME has a sequence similar to that of a PME that is obtainable from the lamella or albedo of an orange, providing the recombinant PME can de-esterify pectin in a block-wise manner.

Preferably, the block-wise enzymatically de-esterified pectin is prepared by treating a pectin with a recombinant enzyme comprising any one of the amino acid sequences shown as SEQ. I.D. No.1 or SEQ. I.D. No. 2, or a variant, derivative or homologue thereof, including combinations thereof.

Preferably, the block-wise enzymatically d-esterified pectin is prepared by treating a pectin with a recombinant enzyme that is obtainable by expression of a nucleotide sequence comprising the nucleotide sequence shown as SEQ. I.D. No. 3 or SEQ. I.D. No. 4, or a variant, derivative or homologue thereof, or combinations thereof.

Preferably, the block-wise enzymatically de-esterified pectin is prepared by treating a pectin with a recombinant enzyme that is obtainable by expression of the PME coding sequence contained in NCIMB 40749 or NCIMB 40750, or a variant, derivative or homologue thereof, or combinations thereof.

Preferably, the block-wise enzymatically de-esterified pectin is prepared by treating the pectin with the recombinant pectin methyl esterase in the presence of sodium ions.

Preferably, the block-wise enzymatically de-esterified pectin prepared by recombinant DNA techniques is prepared by treating the pectin with the recombinant pectin methyl esterase in the presence of NaCl, NaNO$_3$ or Na$_2$SO$_4$.

Preferably the recombinant enzyme comprises all of the sequence shown as SEQ. I.D. No. 1 or SEQ. I.D. No. 2.

Preferably the recombinant enzyme is expressed by a nucleotide sequence that comprises all of the sequence shown as SEQ. I.D. No. 3 or SEQ. I.D. No. 4.

The present invention also covers sequences that are complementary to the aforementioned sequences.

The term "pectin" includes pectin in its normal sense, as well as fractionates and derivatives thereof, as well as modified pectins (e.g. chemically modified pectins and enzymatically modified pectins).

Preferably, the pectin is not a pectin that has been prior treated with the enzyme polygalacturonase to substantially reduce the length of the pectin backbone.

The terms "variant", "homologue" or "fragment" in relation to the recombinant enzyme of the present invention include any substitution of, variation of, modification of, replacement of, deletion of or addition of one (or more) amino acid from or to the sequence providing the resultant amino acid sequence has PME activity, preferably having at least the same activity of a recombinant enzyme comprising any one or more of the sequences shown as SEQ I.D. No.s 1 and 2. In particular, the term "homologue" covers homology with respect to structure and/or function providing the resultant recombinant enzyme has PME activity. With respect to sequence homology (i.e. similarity), preferably there is at least 75%. more preferably at least 85%. more preferably at least 90% homology to the sequences shown in the attached sequence listings. More preferably there is at least 95%, more preferably at least 98%, homology to the sequences shown in the attached sequence listings.

The terms "variant", "homologue" or "fragment" in relation to the nucleotide sequence coding for the recombinant enzyme of the present invention include any substitution of, variation of, modification of, replacement of, deletion of or addition of one (or more) nucleic acid from or to the sequence providing the resultant nucleotide sequence codes for a recombinant enzyme having PME activity, preferably having at least the same activity of a recombinant enzyme comprising any one or more of the sequences shown as SEQ I.D. No.s 1 and 2. In particular, the term "homologue" covers homology with respect to structure and/or function providing the resultant nucleotide sequence codes for a recombinant enzyme having PME activity. With respect to sequence homology (i.e. similarity), preferably there is at least 75%, more preferably at least 85%, more preferably at least 90% homology. More preferably there is at least 95%, more preferably at least 98%, homology.

The above terms are synonymous with allelic variations of the sequences.

The term "complementary" means that the present invention also covers nucleotide sequences that can hybridise to the nucleotide sequences of the coding sequence.

The term "nucleotide" in relation to the present invention includes genomic DNA, cDNA, synthetic DNA, and RNA. Preferably it means DNA, more preferably cDNA for the coding sequence of the present invention.

The term "citrus fruit" means species of the genus Citrus and includes lime, lemon, orange, grapefruit, kumquat, pomelo, and mandarin. Preferably, it means orange.

The term "construct"—which is synonymous with terms such as "conjugate", "cassette" and "hybrid"—includes the nucleotide sequence according to the present invention or, the case of the combination of constructs, the GOI directly or indirectly attached to a promoter. An example of an indirect attachment is the provision of a suitable spacer group such as an intron sequence, such as the Sh1-intron or the ADH intron, intermediate the promoter and the nucleotide sequence of the present invention or the GOI. The same is true for the term "fused" in relation to the present invention which includes direct or indirect attachment. In each case, the terms do not cover the natural combination of the gene coding for the enzyme ordinarily associated with the wild type gene promoter and when they are both in their natural environment.

The construct may even contain or express a marker which allows for the selection of the genetic construct in, for example, a filamentous fungus, preferably of the genus *Aspergillus*, such as *Aspergillus niger*, or plants, such as potatoes, sugar beet etc., into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

The term "vector" includes expression vectors and transformation vectors.

The term "expression vector" means a construct capable of in vivo or in vitro expression.

The term "transformation vector" means a construct capable of being transferred from one species to another—such as from an *E. coli* plasmid to a filamentous fungus, preferably of the genus *Aspergillus*. It may even be a construct capable of being transferred from an *E. coli* plasmid to an *Agrobacterium* to a plant.

The term "tissue" includes tissue per se and organ.

The term "organism" in relation to the present invention includes any organism that could comprise the nucleotide sequence coding for the recombinant enzyme according to the present invention and/or products obtained therefrom, wherein a promoter can allow expression of the nucleotide sequence according to the present invention when present in the organism.

Preferably the organism is a filamentous fungus, preferably of the genus *Aspergillus*, more preferably *Aspergillus niger*.

The term "transgenic organism" in relation to the present invention includes any organism that comprises the nucleotide sequence coding for the recombinant enzyme according to the present invention and/or products obtained therefrom, wherein the promoter can allow expression of the nucleotide sequence according to the present invention within the organism. Preferably the nucleotide sequence is incorporated in the genome of the organism.

Preferably the transgenic organism is a filamentous fungus, preferably of the genus *Aspergillus*, more preferably *Aspergillus niger*.

Therefore, the transgenic organism of the present invention includes an organism comprising any one of, or combinations of, a promoter, the nucleotide sequence coding for the recombinant enzyme according to the present invention, constructs according to the present invention (including combinations thereof), vectors according to the present invention, plasmids according to the present invention, cells according to the present invention, tissues according to the present invention or the products thereof.

The term "transgenic organism" does not cover the native nucleotide coding sequence according to the present invention in its natural environment when it is under the control of its native promoter which is also in its natural environment. In addition, the present invention does not cover the native enzyme according to the present invention when it is in its natural environment and when it has been expressed by its native nucleotide coding sequence which is also in its natural environment and when that nucleotide sequence is under the control of its native promoter which is also in its natural environment.

The transformed cell or organism could prepare acceptable quantities of the desired compound which would be easily retrievable from the cell or organism.

Preferably the construct of the present invention comprises the nucleotide sequence of the present invention and a promoter.

The term "promoter" is used in the normal sense of the art, e.g. an RNA polymerase binding site in the Jacob-Monod theory of gene expression.

In one aspect, the nucleotide sequence according to the present invention is under the control of a promoter that may be a cell or tissue specific promoter. If, for example, the organism is a plant then the promoter can be one that affects expression of the nucleotide sequence in any one or more of tuber, stem, sprout, root and leaf tissues.

By way of example, the promoter for the nucleotide sequence of the present invention can be the α-Amy 1 promoter (otherwise known as the Amy 1 promoter, the Amy 637 promoter or the α-Amy 637 promoter) as described in our co-pending UK patent application No. 9421292.5 filed Oct. 21, 1994. Alternatively, the promoter for the nucleotide sequence of the present invention can be the α-Amy 3 promoter (otherwise known as the Amy 3 promoter, the Amy 351 promoter or the α-Amy 351 promoter) as described in our co-pending UK patent application No. 9421286.7 filed Oct. 21, 1994.

The promoter could additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention or, in the case of the combination of constructs, the GOI. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

In addition the present invention also encompasses combinations of promoters and/or nucleotide sequences coding for proteins or recombinant enzymes and/or elements.

The present invention also encompasses the use of promoters to express a nucleotide sequence coding for the recombinant enzyme according to the present invention or the GOI, wherein a part of the promoter is inactivated but wherein the promoter can still function as a promoter. Partial inactivation of a promoter in some instances is advantageous. In particular, with the Amy 351 promoter mentioned earlier it is possible to inactivate a part of it so that the partially inactivated promoter expresses the nucleotide of the present invention or a GOI in a more specific manner such as in just one specific tissue type or organ.

The term "inactivated" means partial inactivation in the sense that the expression pattern of the promoter is modified but wherein the partially inactivated promoter still functions as a promoter. However, as mentioned above, the modified promoter is capable of expressing the nucleotide of the present invention or a GOI in at least one (but not all) specific tissue of the original promoter. One such promoter is the Amy 351 promoter described above. Examples of partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part. Another modification is to mutate the binding sites for regulatory proteins for example the CreA protein known from filamentous fungi to exert carbon catabolite repression, and thus abolish the catabolite repression of the native promoter.

The term "GOI" with reference to the combination of constructs according to the present invention means any gene of interest. A GOI can be any nucleotide that is either foreign or natural to the organism (e.g. filamentous fungus, preferably of the genus *Aspergillus*, or a plant) in question. Typical examples of a GOI include genes encoding for proteins and enzymes that modify metabolic and catabolic processes. The GOI may code for an agent for introducing or increasing pathogen resistance. The GOI may even be an antisense construct for modifying the expression of natural transcripts present in the relevant tissues. The GOI may even code for a non-native protein of a filamentous fungus, preferably of the genus *Aspergillus*, or a compound that is of benefit to animals or humans.

Examples of GOIs include other pectinases, pectin depolymerases, polygalacturonases, pectate lyases, pectin lyases, rhamno-galacturonases, hemicellulases, endo-β-glucanases, arabinases, or acetyl esterases, or combinations thereof, as well as antisense sequences thereof.

The GOI may be a protein giving nutritional value to a food or crop. Typical examples include plant proteins that can inhibit the formation of anti-nutritive factors and plant proteins that have a more desirable amino acid composition (e.g. a higher lysine content than a non-transgenic plant). The GOI may even code for an enzyme that can be used in food processing such as chymosin, thaumatin and α-galactosidase. The GOI can be a gene encoding for any one of a pest toxin, an antisense transcript such as that for patatin or α-amylase, ADP-glucose pyrophosphorylase (e.g. see EP-A-0455316), a protease antisense, a glucanase or genomic PME.

The GOI may even code for an intron of a particular enzyme but wherein the intron can be in sense or antisense orientation. In the latter instance, the particular enzyme could be genomic PME. Antisense expression of genomic exon or intron sequences as the GOI would mean that the natural PME expression would be reduced or eliminated but wherein the recombinant PME expression would not be affected. This is particularly true for antisense intron or sense intron expression.

The GOI can be the nucleotide sequence coding for the α-amylase enzyme which is the subject of our co-pending UK patent application 9413439.2 filed on Jul. 4, 1994. The GOI can be the nucleotide sequence coding for the α-amylase enzyme which is the subject of our co-pending UK patent application 9421290.9 filed on 21 Oct. 1994. The GOI can be any of the nucleotide sequences coding for the ADP-glucose pyrophosphorylase enzymes which are the subject of our co-pending PCT patent application PCT/EP94/01082 filed 7 Apr. 1994. The GOI can be any of the nucleotide sequences coding for the α-glucanlyase enzyme which are described in our co-pending PCT patent application PCT/EP94/03397 filed 15 Oct. 1994.

The host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor laboratory Press). If a prokaryotic host is used then the gene may need to be suitably modified before transformation—such as by removal of introns.

As mentioned above, a preferred host organism is of the genus *Aspergillus*, such as *Aspergillus niger*.

A transgenic *Aspergillus* according to the present invention can be prepared by following the teachings of Rambosek, J. and Leach, J. 1987 (Recombinant DNA in filamentous fungi: Progress and Prospects. CRC Crit. Rev. Biotechnol. 6:357–393), Davis R. W. 1994 (Heterologous gene expression and protein secretion in *Aspergillus*. In: Martinelli S. D., Kinghorn J. R.(Editors) *Aspergillus:* 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong, S. A., Berka R. M. (Editors) Molecular Industrial Mycology Systems and Applications for Filamentous Fungi. Marcel Dekker Inc. New York 1991. pp 1–29) and Turner G. 1994 (Vectors for genetic manipulation. In: Martinelli S. D., Kinghorn J. R.(Editors) *Aspergillus:* 50 years on. Progress in industrial microbiology vol 29. Elsevier Amsterdam 1994. pp. 641–666). However, the following commentary provides a summary of those teachings for producing transgenic *Aspergillus* according to the present invention.

For almost a century, filamentous fungi have been widely used in many types of industry for the production of organic compounds and enzymes. For example, traditional japanese koji and soy fermentations have used *Aspergillus* sp. Also, in this century *Aspergillus niger* has been used for production of organic acids particular citric acid and for production of various enzymes for use in industry.

There are two major reasons why filamentous fungi have been so widely used in industry. First filamentous fungi can produce high amounts of extracelluar products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous expression according to the present invention.

In order to prepare the transgenic *Aspergillus*, expression constructs are prepared by inserting the nucleotide sequence according to the present invention (or even the GOI) into a construct designed for expression in filamentous fungi.

Several types of constructs used for heterologous expression have been developed. These constructs preferably contain a promoter which is active in fungi. Examples of promoters include a fungal promoter for a highly expressed extracelluar enzyme, such as the glucoamylase promoter or the α-amylase promoter. The nucleotide sequence according to the present invention (or even the GOI) can be fused to a signal sequence which directs the protein encoded by the nucleotide sequence according to the present invention (or even the GOI) to be secreted. Usually a signal sequence of fungal origin is used. A terminator active in fungi ends the expression system.

Another type of expression system has been developed in fungi where the nucleotide sequence according to the present invention (or even the GOI) can be fused to a smaller or a larger part of a fungal gene encoding a stable protein. This can stabilize the protein encoded by the nucleotide sequence according to the present invention (or even the GOI). In such a system a cleavage site, recognized by a specific protease, can be introduced between the fungal protein and the protein encoded by the nucleotide sequence according to the present invention (or even the GOI), so the produced fusion protein can be cleaved at this position by the specific protease thus liberating the protein encoded by the nucleotide sequence according to the present invention (or even the GOI). By way of example, one can introduce a site which is recognized by a KEX-2 like peptidase found in at least some *Aspergilli*. Such a fusion leads to cleavage in vivo resulting in protection of the expressed product and not a larger fusion protein.

Heterologous expression in *Aspergillus* has been reported for several genes coding for bacterial, funzal, vertebrate and plant proteins. The proteins can be deposited intracellularly if the nucleotide sequence according to the present invention (or even the GOI) is not fused to a signal sequence. Such proteins will accumulate in the cytoplasm and will usually not be glycosylated which can be an advantage for some bacterial proteins. If the nucleotide sequence according to the present invention (or even the GOI) is equipped with a signal sequence the protein will accumulate extracelluarly.

With regard to product stability and host strain modifications, some heterologous proteins are not very stable when they are secreted into the culture fluid of fungi. Most fungi produce several extracelluar proteases which degrade heterologous proteins. To avoid this problem special fungal strains with reduced protease production have been used as host for heterologous production.

For the transformation of filamentous fungi, several transformation protocols have been developed for many filamentous fungi (Ballance 1991, ibid). Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A commonly used transformation marker is the amdS gene of *A. nidulans* which in high copy number allows the fungus to grow with acrylamide as the sole nitrogen source.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et at (1987, Yeast Biotechnology, D R Berry et al, eds, pp 401–429, Allen and Unwin, London) and by King et al. (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevsiae.*

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press IAd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed.

For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275. 104); and Ito, H et al (1983, J Bacteriology 153, 163–168).

The transformed yeast cells are selected using various selective markers. Among the markers used for transformation are a number of auxotmphic markers such as LEU2, HIS4 and TRP1, and dominant antibiotic resistance markers such as aminoglycoside antibiotic markers, eg G418.

Another host organism is a plant.

Even though the enzyme and the nucleotide sequence coding therefor are not disclosed in EP-B-0470145 and CA-A-2006454, those two documents do provide some useful background commentary on the types of techniques that may be employed to prepare transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual A*3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists*, eds.: D. S. Ingrams and J. P. Helgeson, 203–208.

Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct. Preferably, the vector system is an *Agrobacterium tumefaciens* Ti-plasmid or an *Agrobacterium rhizogenes* Ri-plasmid or a derivative thereof, as these plasmids are well-known and widely employed in the construction of transgenic plants, many vector systems exist which are based on these plasmids or derivatives thereof.

In the construction of a transgenic plant the nucleotide sequence or construct of the present invention may be first constructed in a microorganism in which the vector can replicate and which is easy to manipulate before insertion into the plant. An example of a useful microorganism is *E. coli*, but other microorganisms having the above properties may be used. When a vector of a vector system as defined above has been constructed in *E. coli*, it is transferred, if necessary, into a suitable *Agrobacterium* strain, e.g. *Agrobacterium tumefaciens*. The Ti-plasmid harbouring the nucleotide sequence or construct of the invention is thus preferably transferred into a suitable *Agrobacterium* strain, e.g. *A. tumefaciens*, so as to obtain an *Agrobacterium* cell harbouring the nucleotide sequence or construct of the invention, which DNA is subsequently transferred into the plant cell to be modified.

As reported in CA-A-2006454, a large amount of cloning vectors are available which contain a replication system in *E. coli* and a marker which allows a selection of the transformed cells. The vectors contain for example pBR 322, the pUC series, the M13 mp series, pACYC 184 etc.

In this way, the nucleotide or construct of the present invention can be introduced into a suitable restriction position in the vector. The contained plasmid is used for the transformation in *E. coli*. The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After each introduction method of the desired promoter or construct or nucleotide sequence according to the present invention in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al. EMBO J. (1985) 4:277–284.

Direct infection of plant tissues by *Agrobacterium* is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be done on a certain part or tissue of the plant, i.e. on a part of a leaf, a root, a stem or another part of the plant.

Typically, with direct infection of plant tissues by *Agrobacterium* carrying the promoter and/or the GOI, a plant to be infected is wounded, e.g. by cutting the plant with a razor or puncturing the plant with a needle or rubbing the plant with an abrasive. The wound is then inoculated with the *Agrobacterium*. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

In summation, the present invention provides a process of stabilising at least one protein in an acidic environment comprising contacting the protein with a block-wise enzymatically de-esterified pectin, in particular a block-wise enzymatically de-esterified pectin prepared by recombinant DNA techniques.

In addition the present invention provides an recombinant enzyme useful in that process.

A preferred embodiment of the present invention relates to a process of stabilising at least one protein in an acidic environment comprising contacting the protein with a block-wise enzymatically de-esterified pectin prepared by recombinant DNA techniques, wherein the block-wise enzymatically de-esterified pectin is prepared by use of a recombinant enzyme, and wherein the recombinant enzyme comprises any one of the amino acid sequences shown as SEQ. I.D. No.1 or SEQ. I.D. No. 2 or a variant, derivative or homologue thereof, including combinations thereof, and has the following characteristics:

1. a molecular weight of from about 36 kD to about 64 kD;
2. a pH optimum of pH 7–8 when measured with 0.5% lime pectin in 0.15 M NaCl;
3. a temperature optimum of at least 50° C.;
4. a temperature stability in the range of from 10°–at least 40° C.;
5. a $K_m$ value of 0.07%;
6. an activity maximum at levels of about 0.25 M NaCl;
7. an activity maximum at levels of about 0.2 M $Na_2SO_4$; and
8. an activity maximum at levels of about 0.3 M $NaNO_3$.

Another preferred embodiment of the present invention relates to a method of block-wise enzymatically de-esterifying a pectin comprising treating the pectin with a recombinant enzyme comprising any one of the amino acid sequences shown as SEQ. I.D. No.1 or SEQ. I.D. No. 2, or a variant, derivative or homologue thereof, including combinations thereof, wherein the recombinant enzyme has the following characteristics:

1. a molecular weight of from about 36 kD to about 64 kD;
2. a pH optimum of pH 7–8 when measured with 0.5% lime pectin in 0.15 M NaCl;
3. a temperature optimum of at least 50° C.;
4. a temperature stability in the range of from 10°–at least 40° C.;
5. a $K_m$ value of 0.07%;
6. an activity maximum at levels of about 0.25 M NaCl;
7. an activity maximum at levels of about 0.2 M $Na_2SO_4$; and
8. an activity maximum at levels of about 0.3 M $NaNO_3$.

Another preferred embodiment of the present invention relates to a recombinant enzyme comprising any one of the amino acid sequences shown as SEQ. I.D. No.1 or SEQ. I.D. No. 2, or a variant, derivative or homologue thereof, including combinations thereof, wherein the recombinant enzyme has the following characteristics:
1. a molecular weight of from about 36 kD to about 64 kD;
2. a pH optimum of pH 7–8 when measured with 0.5% lime pectin in 0.15 M NaCl;
3. a temperature optimum of at least 50° C.;
4. a temperature stability in the range of from 10°–at least 40° C.;
5. a $K_m$ value of 0.07%;
6. an activity maximum at levels of about 0.25 M NaCl;
7. an activity maximum at levels of about 0.2 M $Na_2S_4$; and
8. an activity maximum at levels of about 0.3 M $NaNO_3$.

More preferred embodiments of the present invention relate to the afore-mentioned preferred process, method and recombinant enzyme, and wherein the recombinant enzyme has been expressed by a nucleotide sequence comprising the sequence shown as SEQ. I.D. No. 3 or SEQ. I.D. No. 4, or a variant, derivative or homologue thereof.

The following sample has been deposited in accordance with the Budapest Treaty at the recognised depositary The National Collections of Industrial and Marine Bacteria Limited (NCIMB) at 23 St Machar Drive, Aberdeen, Scotland, AB2 IRY, United Kingdom, on 6 Jul. 1995: NCIMB 40749 (which corresponds to plasmid pO34).

The following sample has been deposited in accordance with the Budapest Treaty at the recognised depositary The National Collections of Industial and Marine Bacteria Limited (NCIMB) at 23 St Machar Drive, Aberdeen, Scotland, AB2 IRY, United Kingdom, on 12 July: NCIMB 40750 (which corresponds to plasmid pO17).

Therefore, more preferred embodiments of the present invention relate to the afore-mentioned process, method and recombinant enzyme and wherein the recombinant enzyme is capable of being expressed by NCIMB 40749 or NCIMB 40750.

The present invention also provides an amino acid sequence comprising the sequence shown as SEQ. I.D. No. 5, or a variant, derivative or homologue thereof, suitable for use in imparting or increasing heat stability to a protein.

In addition, the present invention provides a nucleotide sequence comprising the sequence shown as SEQ. I.D. No. 6, or a variant, derivative or homologue thereof, suitable for use in expressing an amino acid sequence for imparting or increasing heat stability to a protein.

With respect to these last aspects, the above commentary for variants, derivatives, homologues, constructs, vectors, transformation of host organisms is equally applicable though of course the amino acid sequence and nucleotide sequence in this case affect the heat stability of proteins.

In this regard, it is believed that the amino acid sequence shown as SEQ. I.D. No. 5 is capable of imparting or increasing the heat stability of a protein, such as the recombinant PME of the present invention. The amino acid sequence may also increase or impart heat stability to other proteins, including PMEs from other sources.

Figure 2:
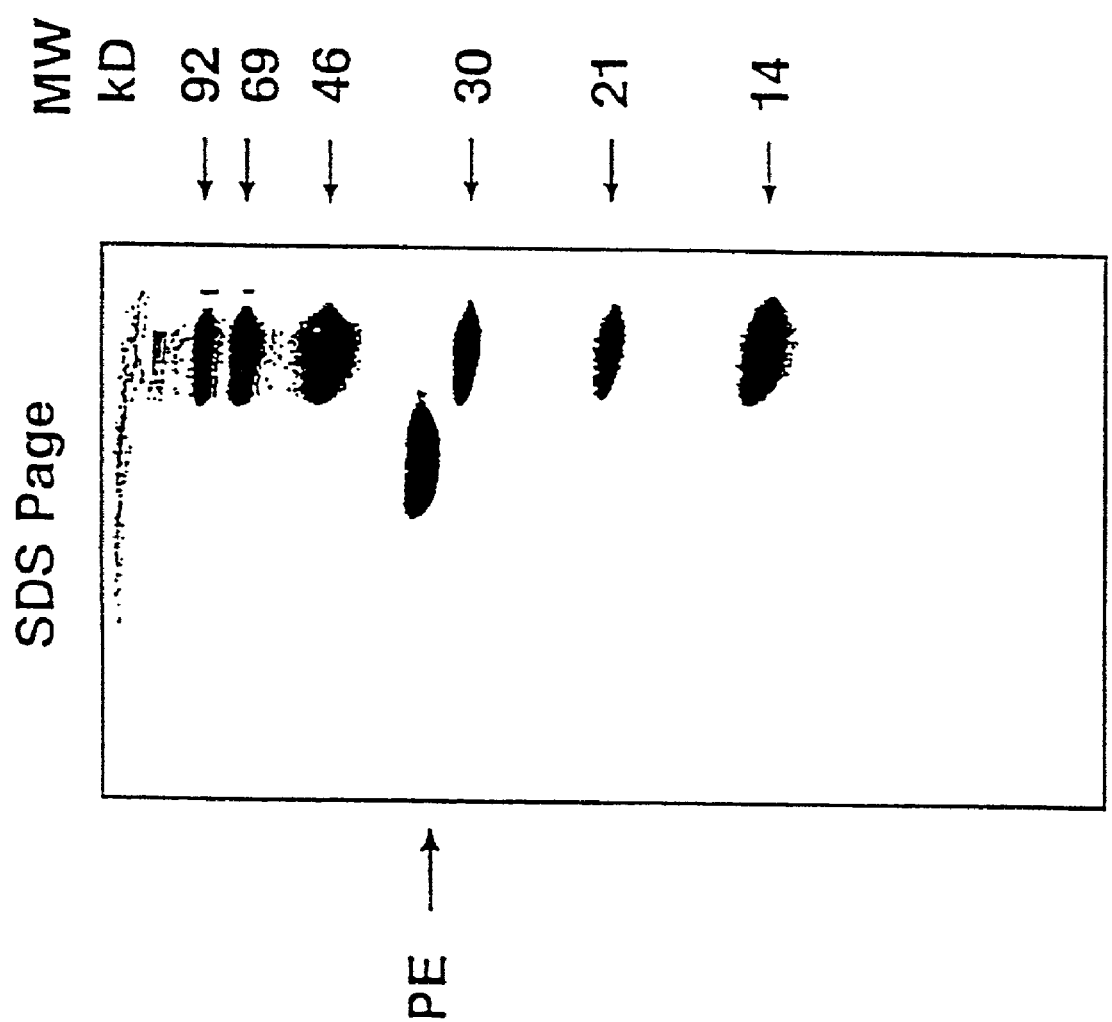
Figure 3:
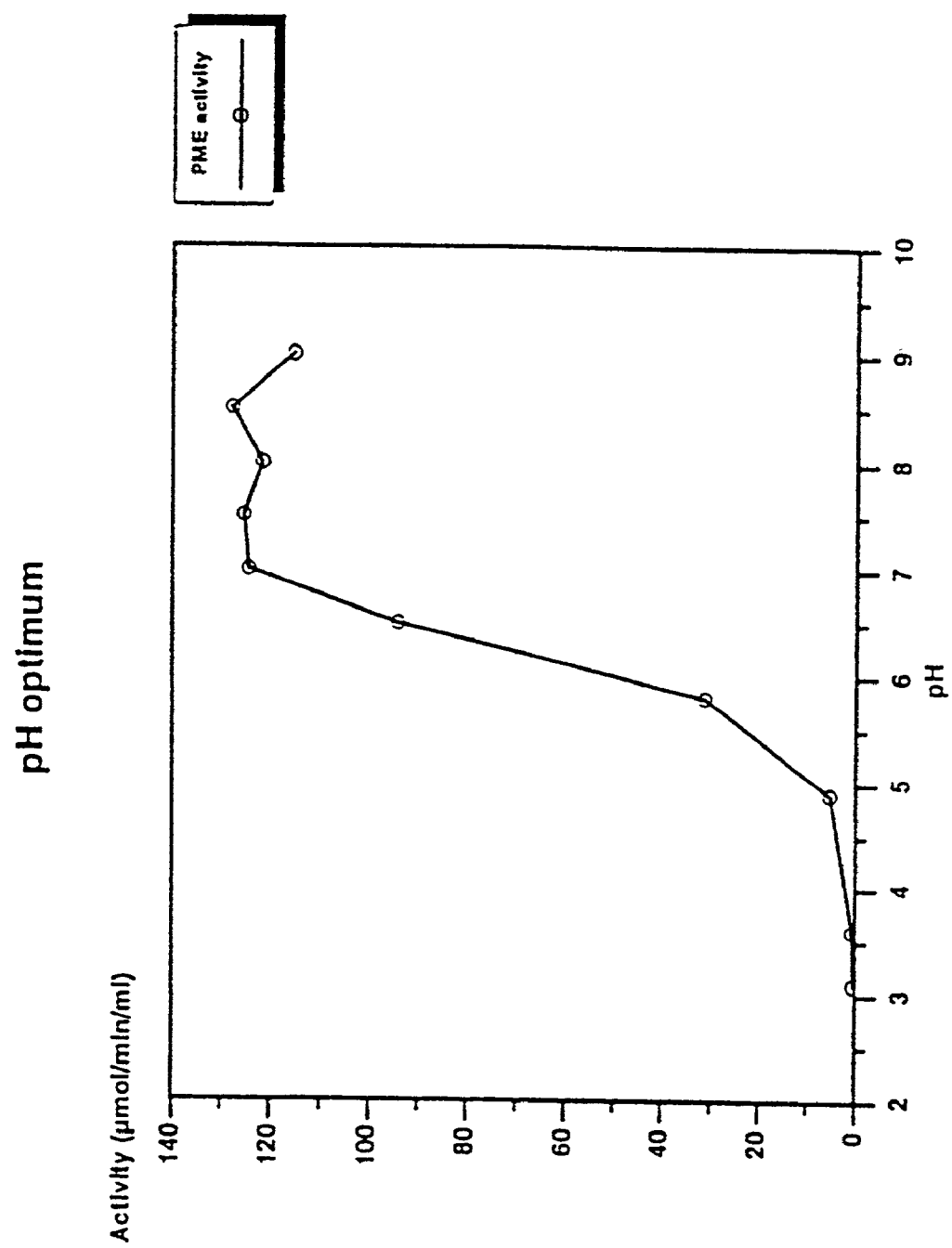
Figure 4:
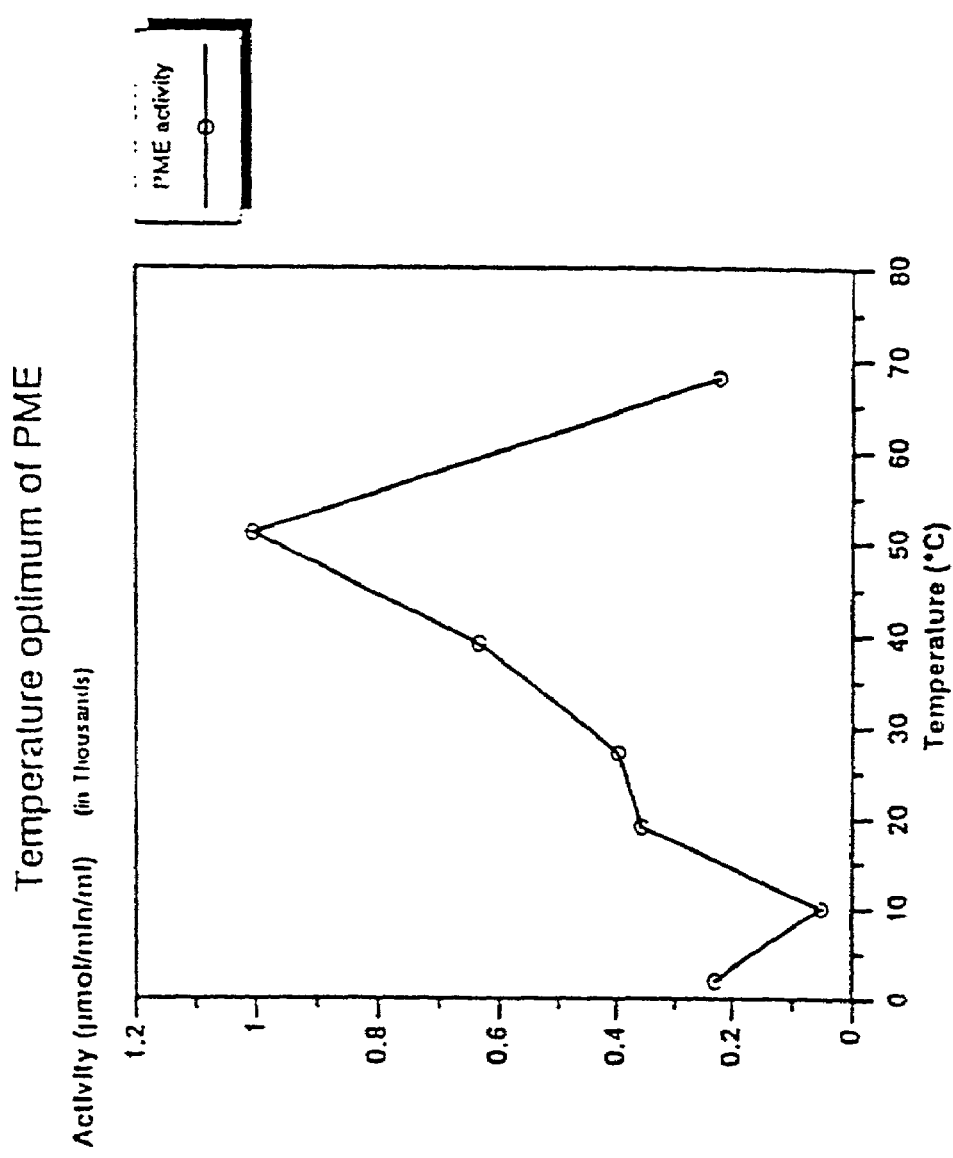
Figure 5:
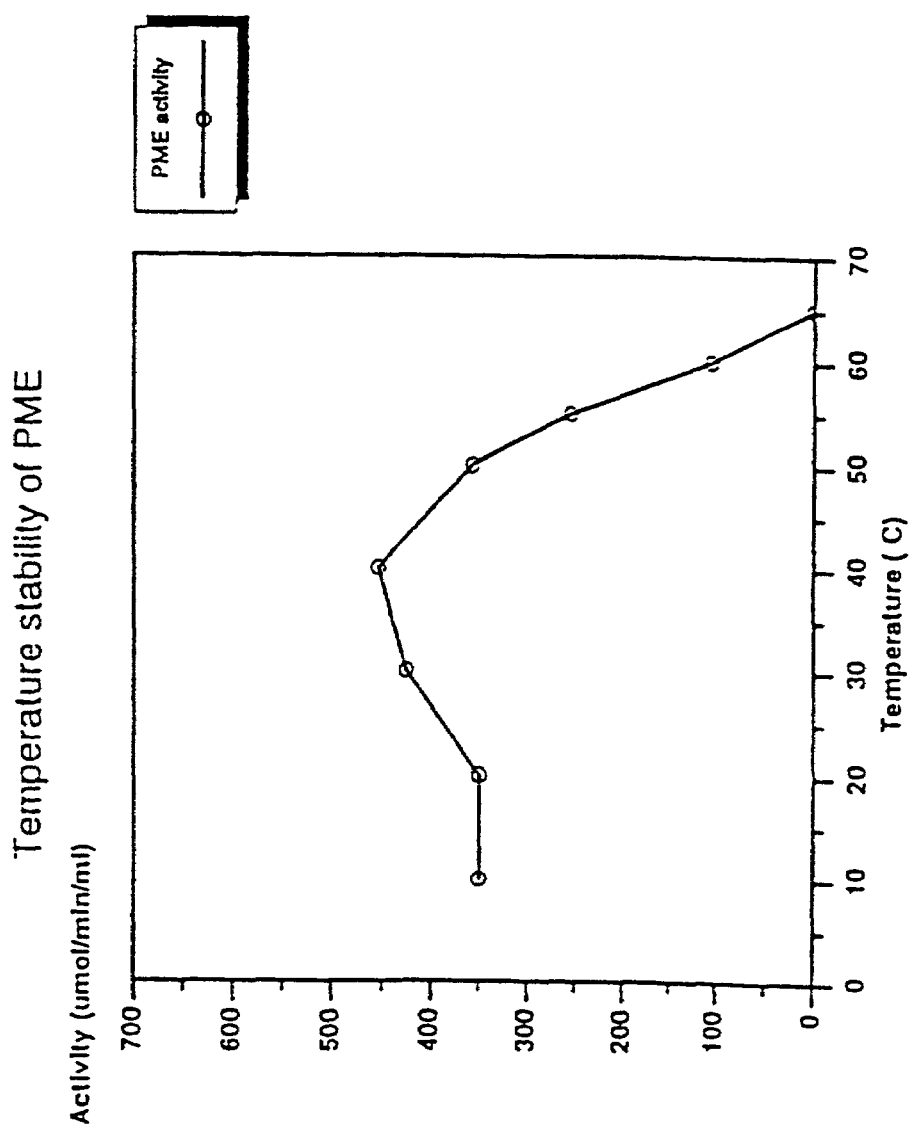
Figure 6:
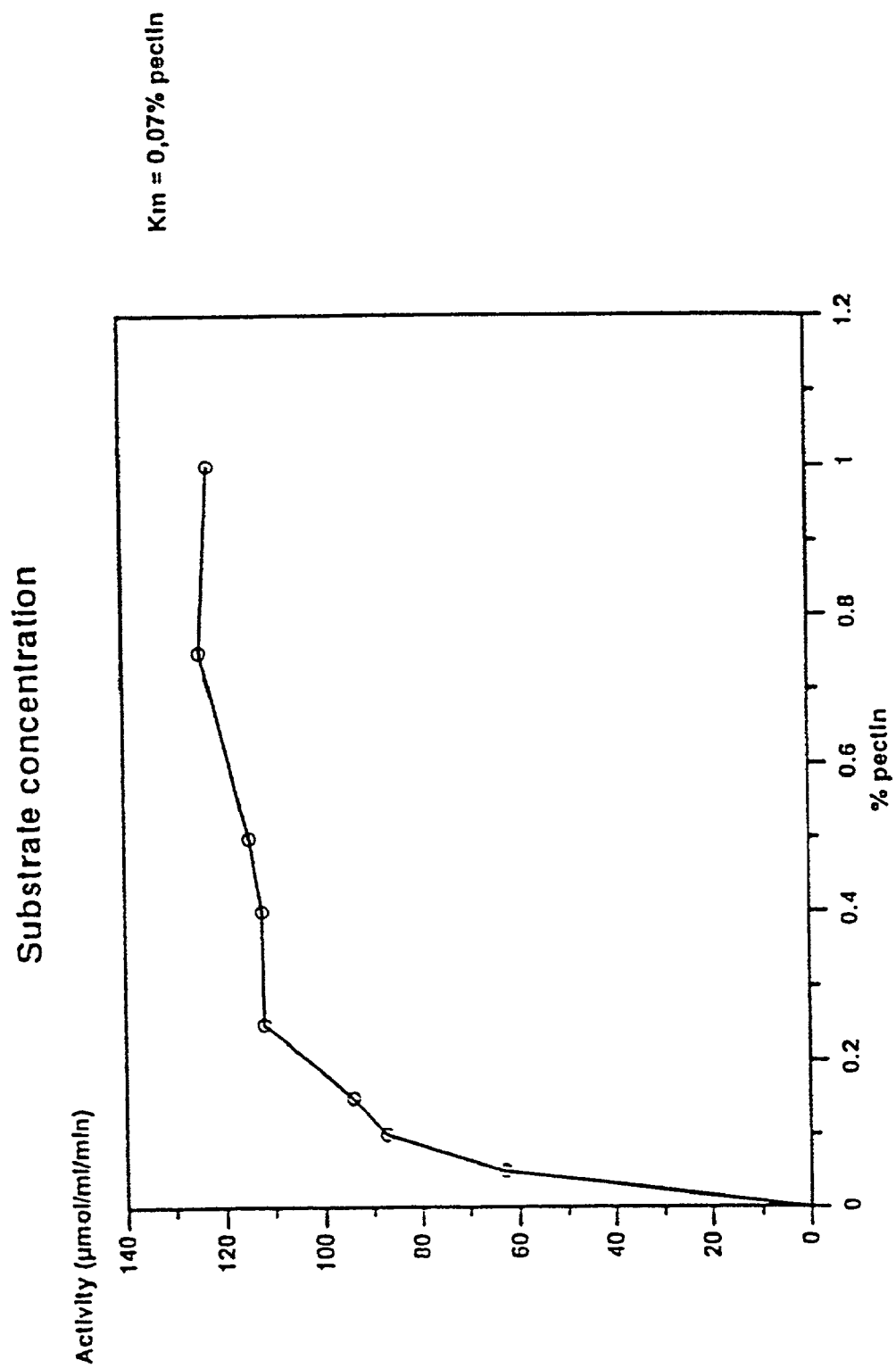
Figure 7:
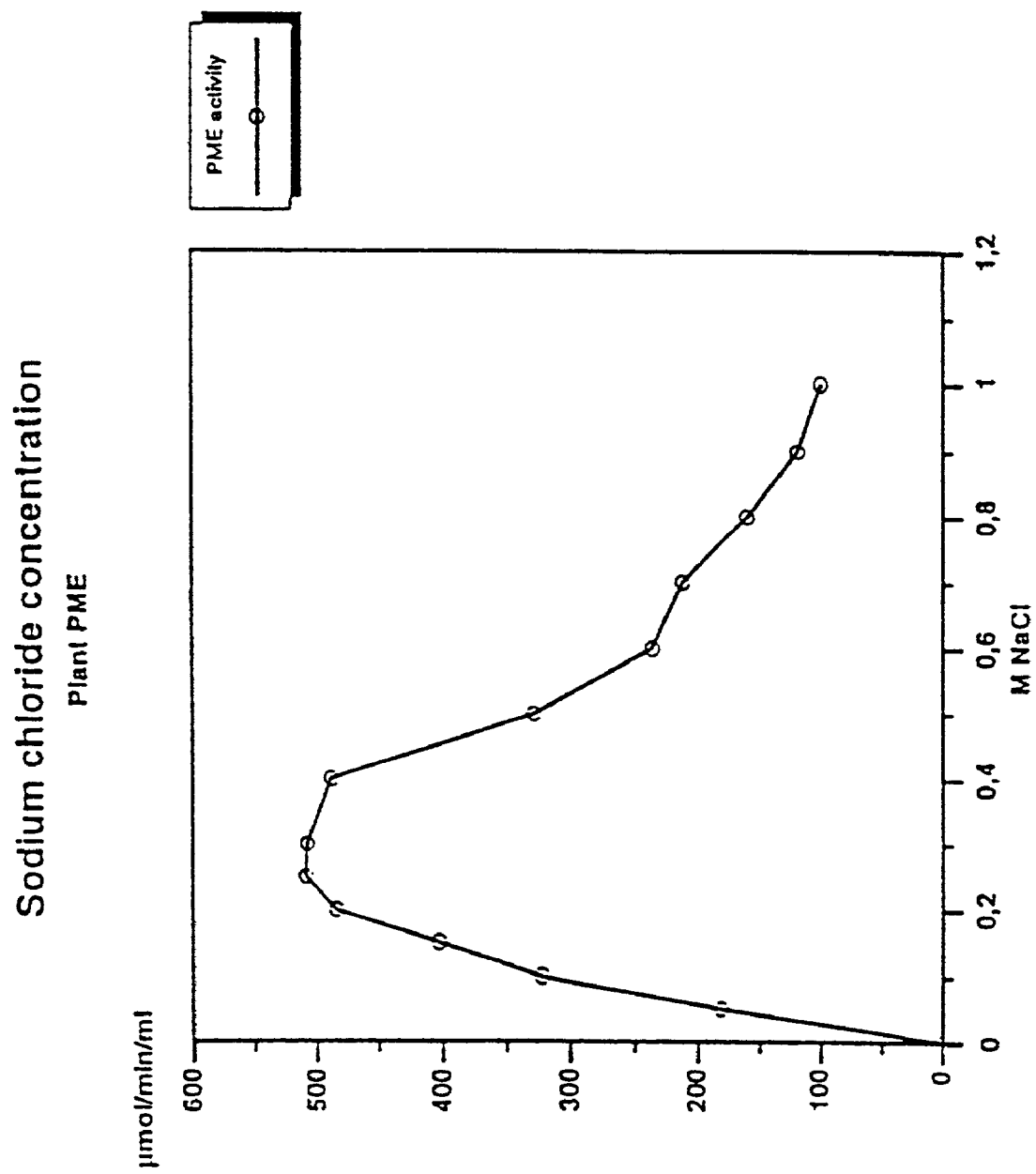
Figure 8:
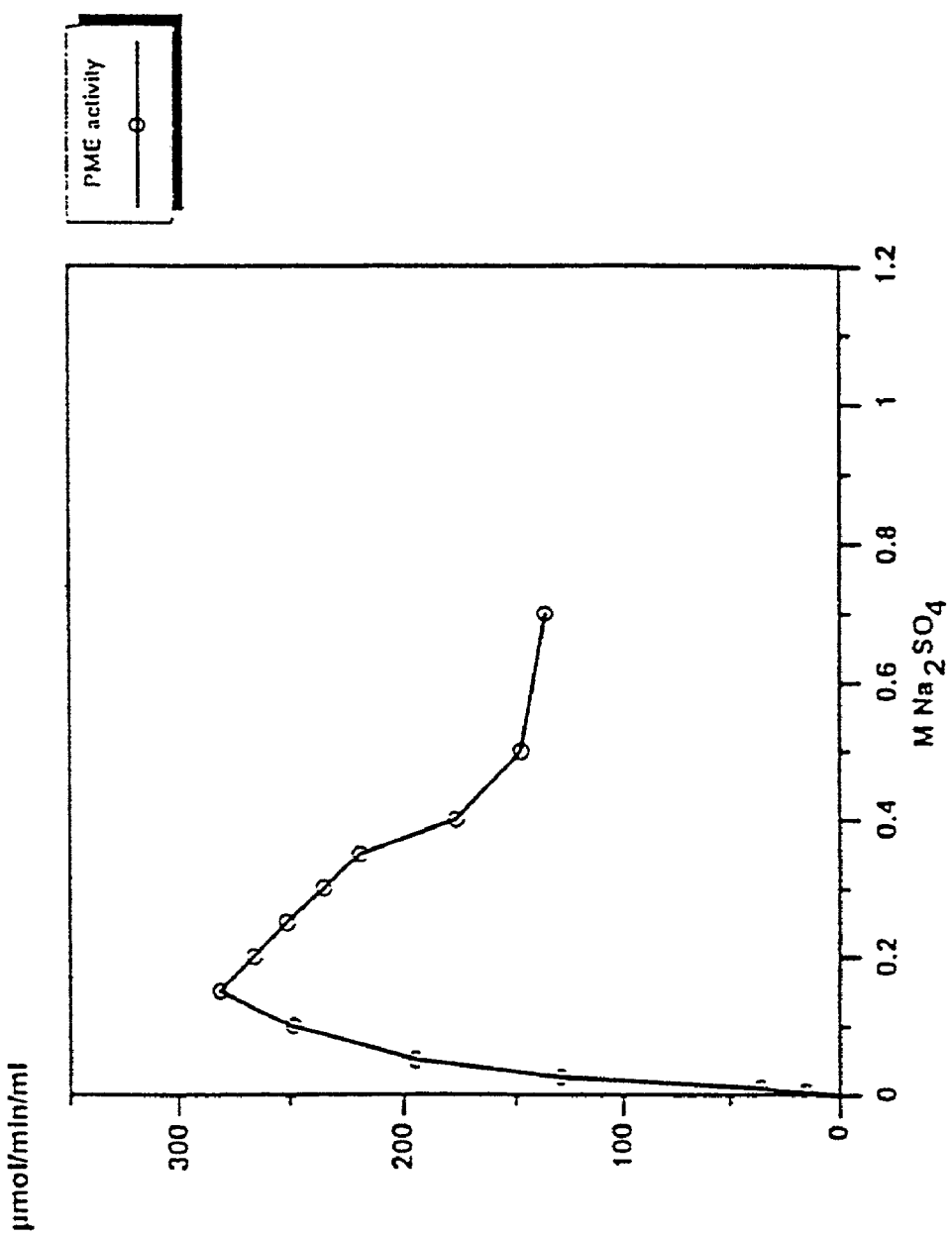
Figure 9:
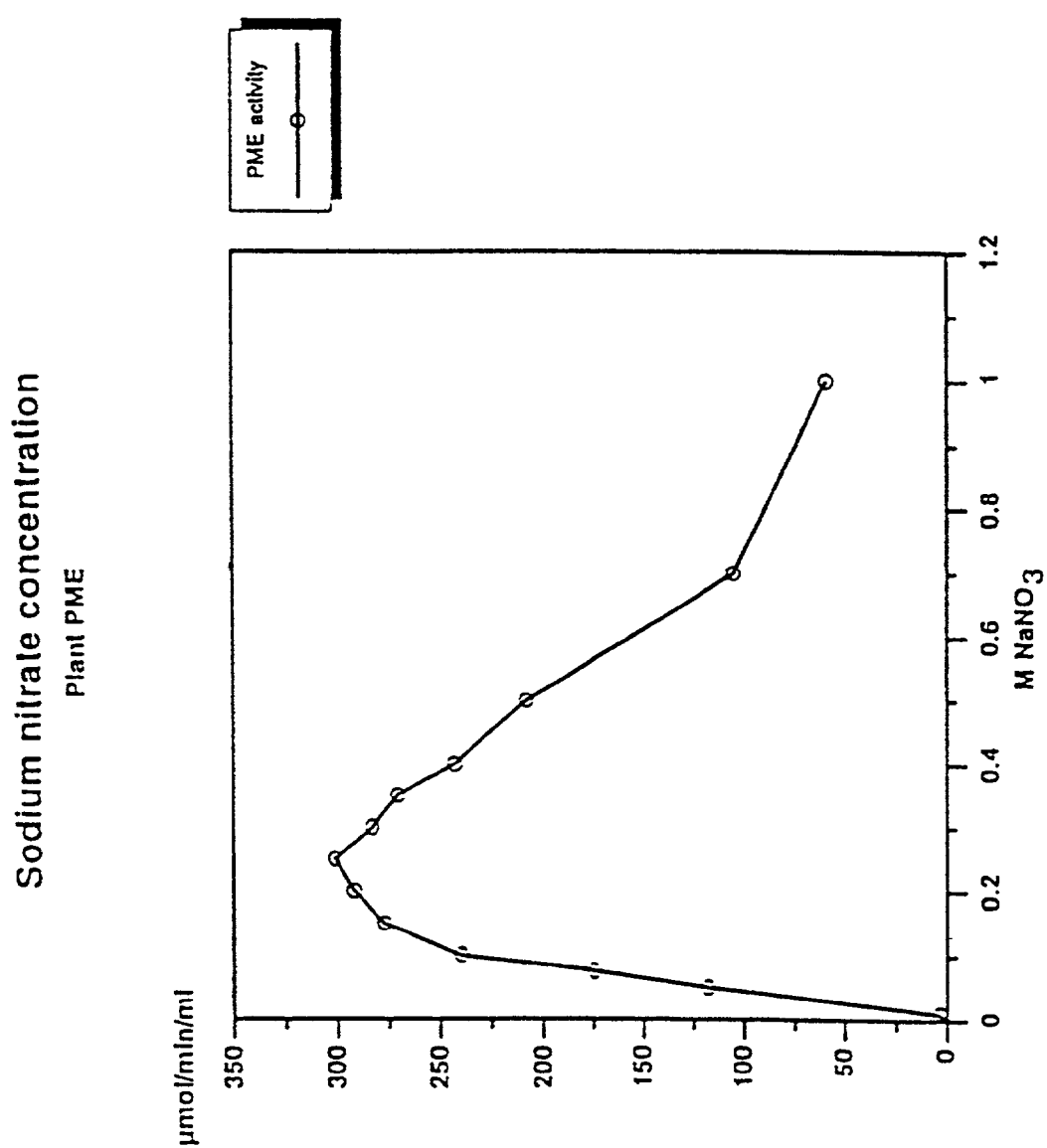
Figure 10:
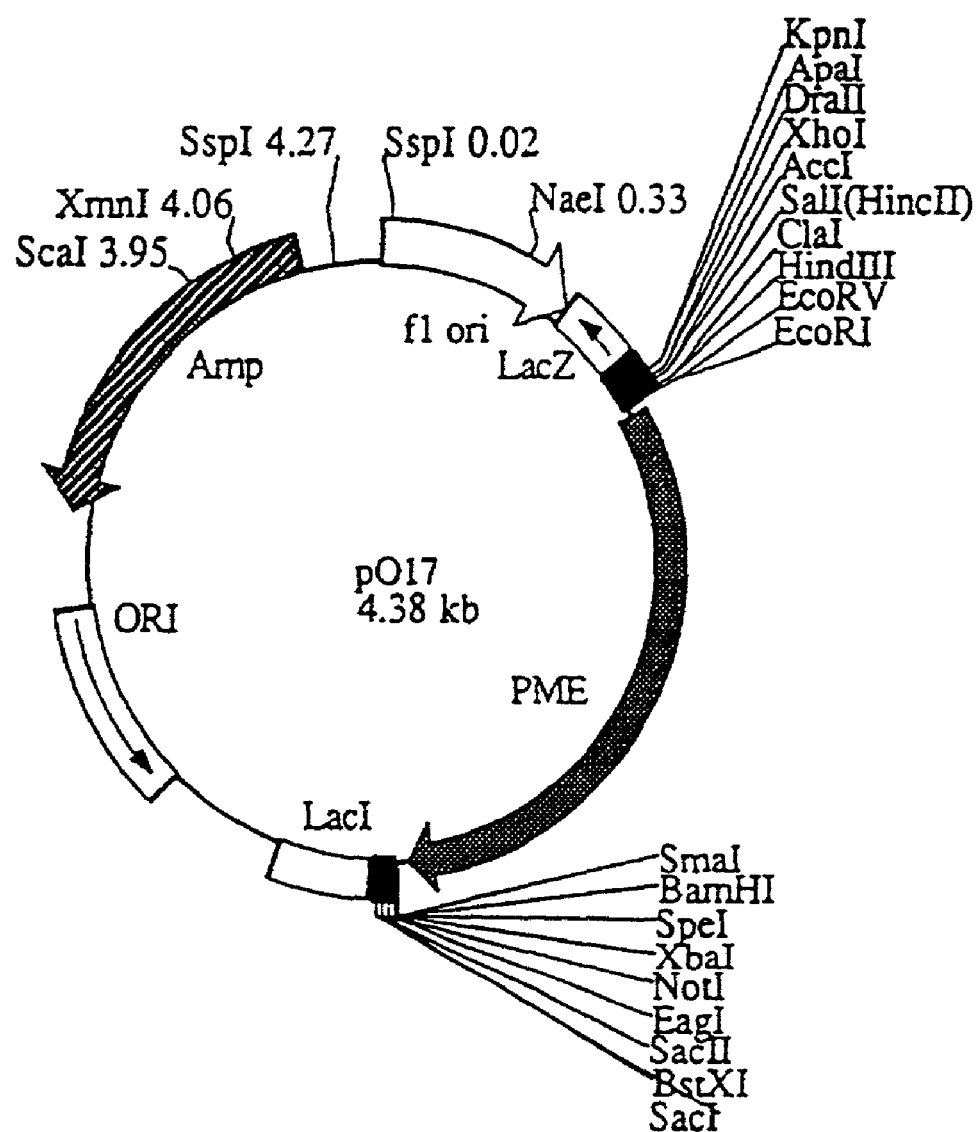
Figure 11:
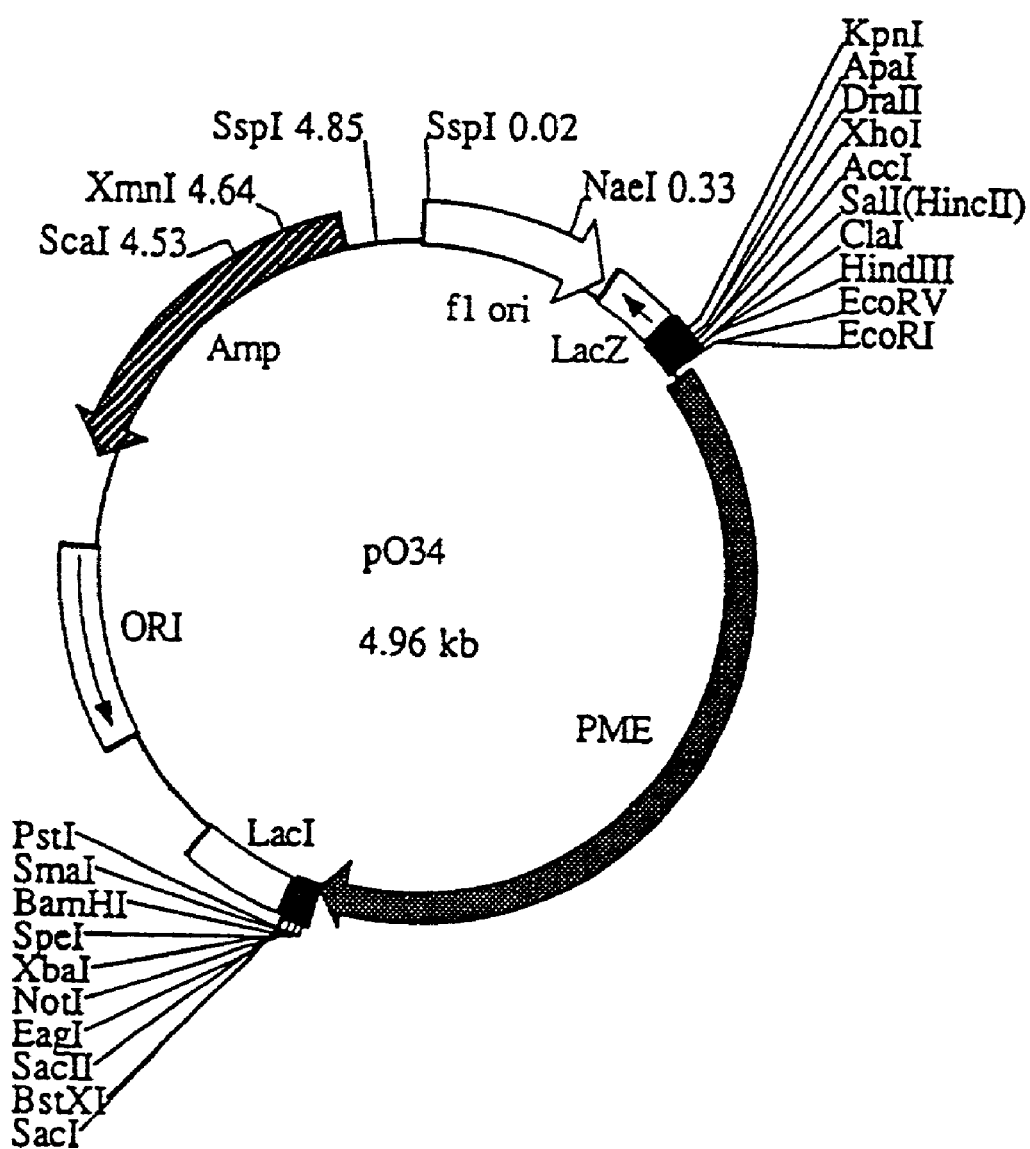
Figure 12:
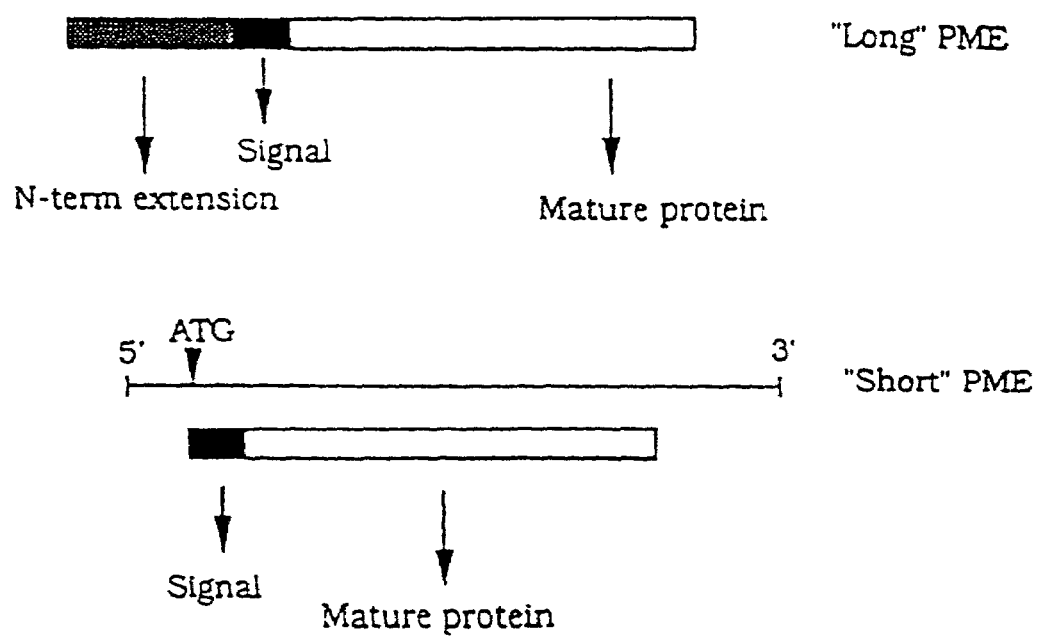
Figure 13:
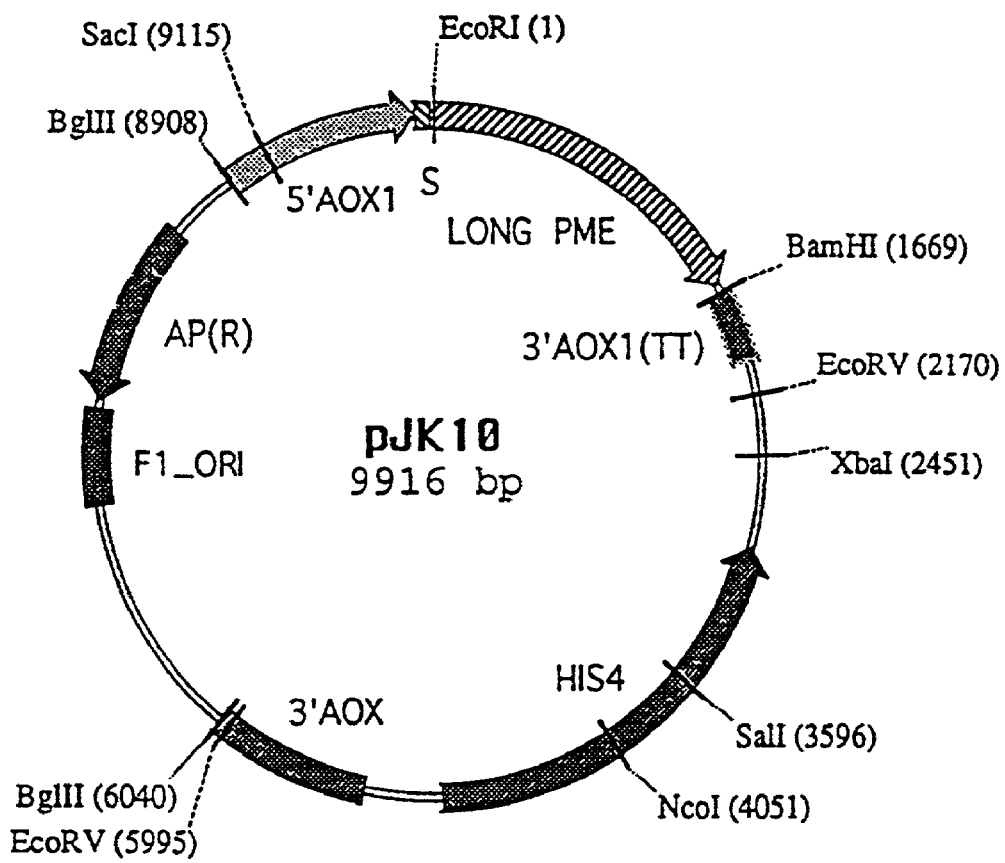
Figure 14:
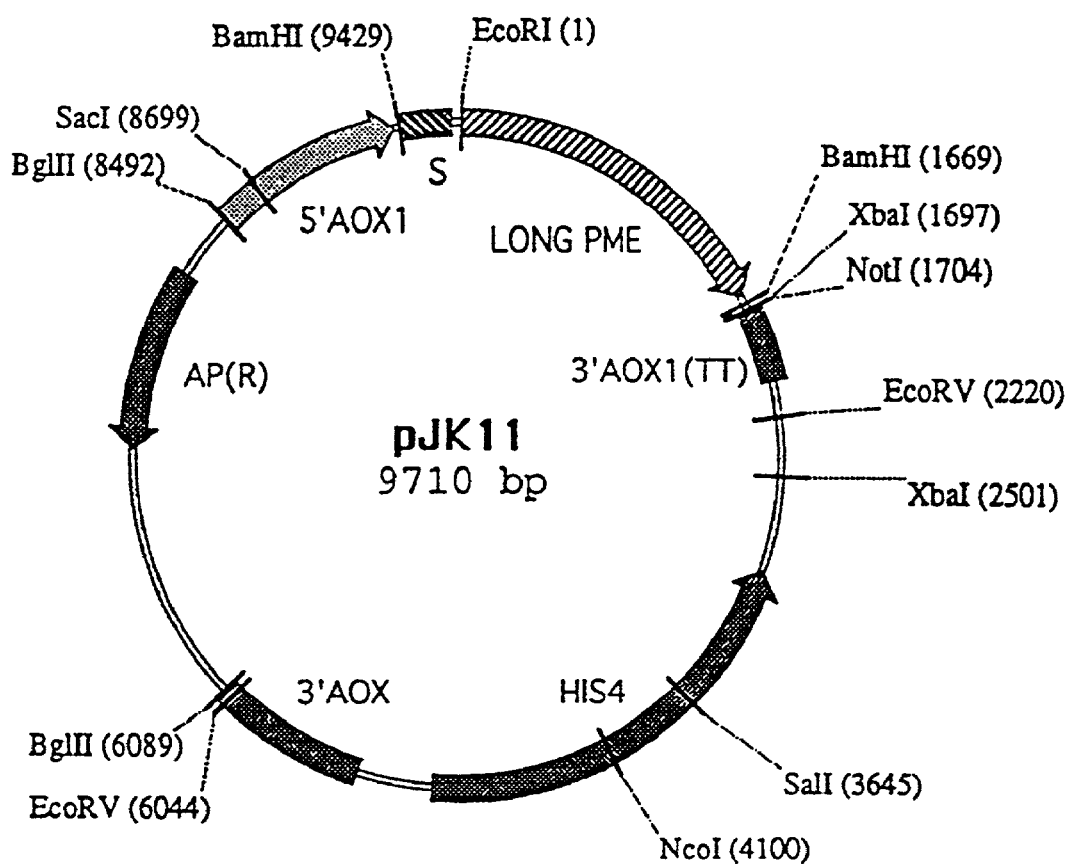
Figure 15:
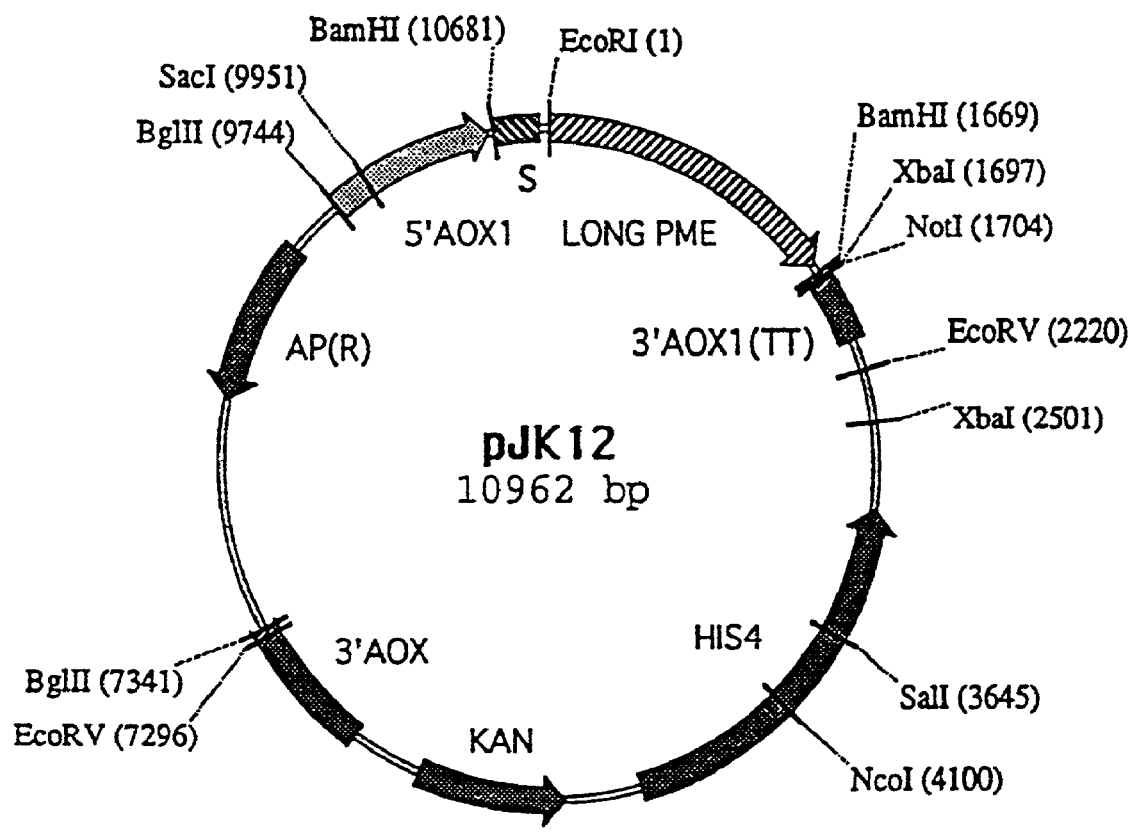
Figure 16:
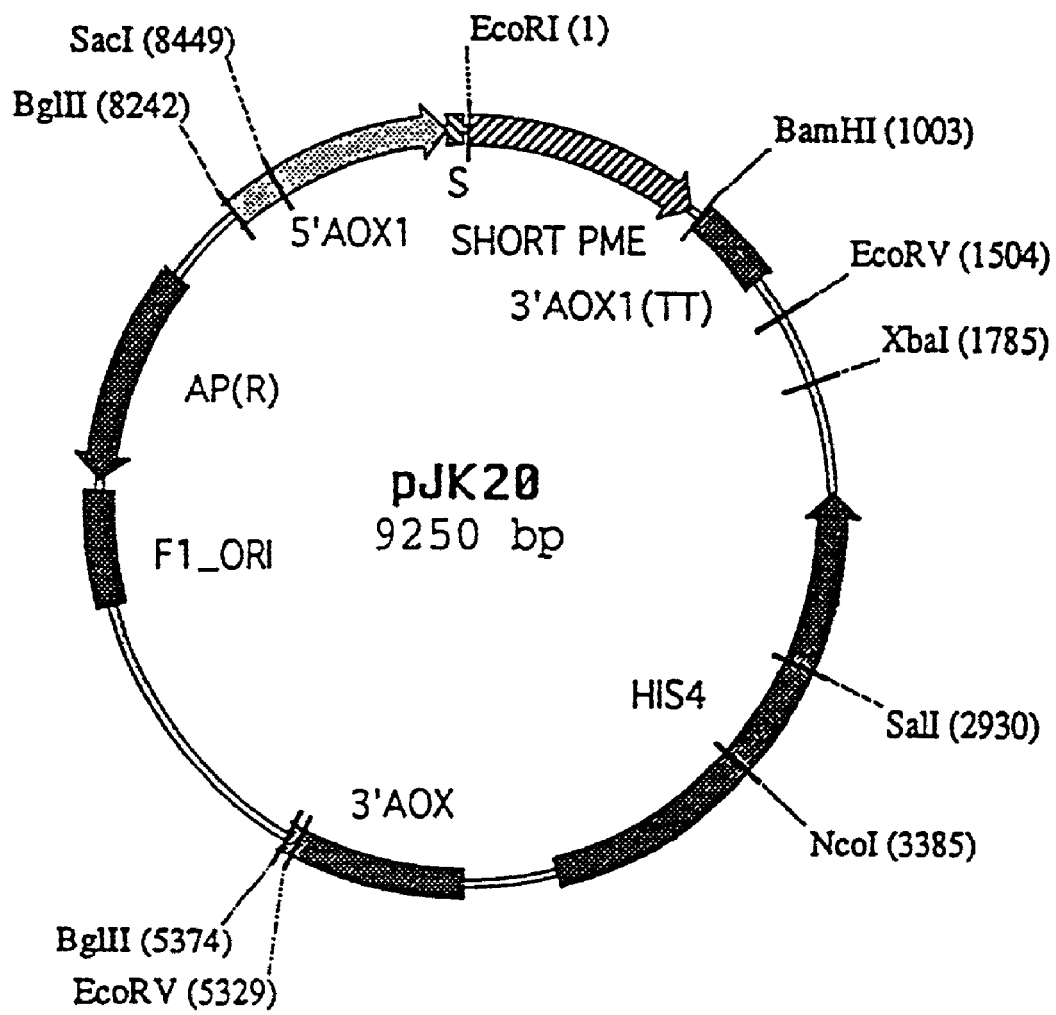
Figure 17:
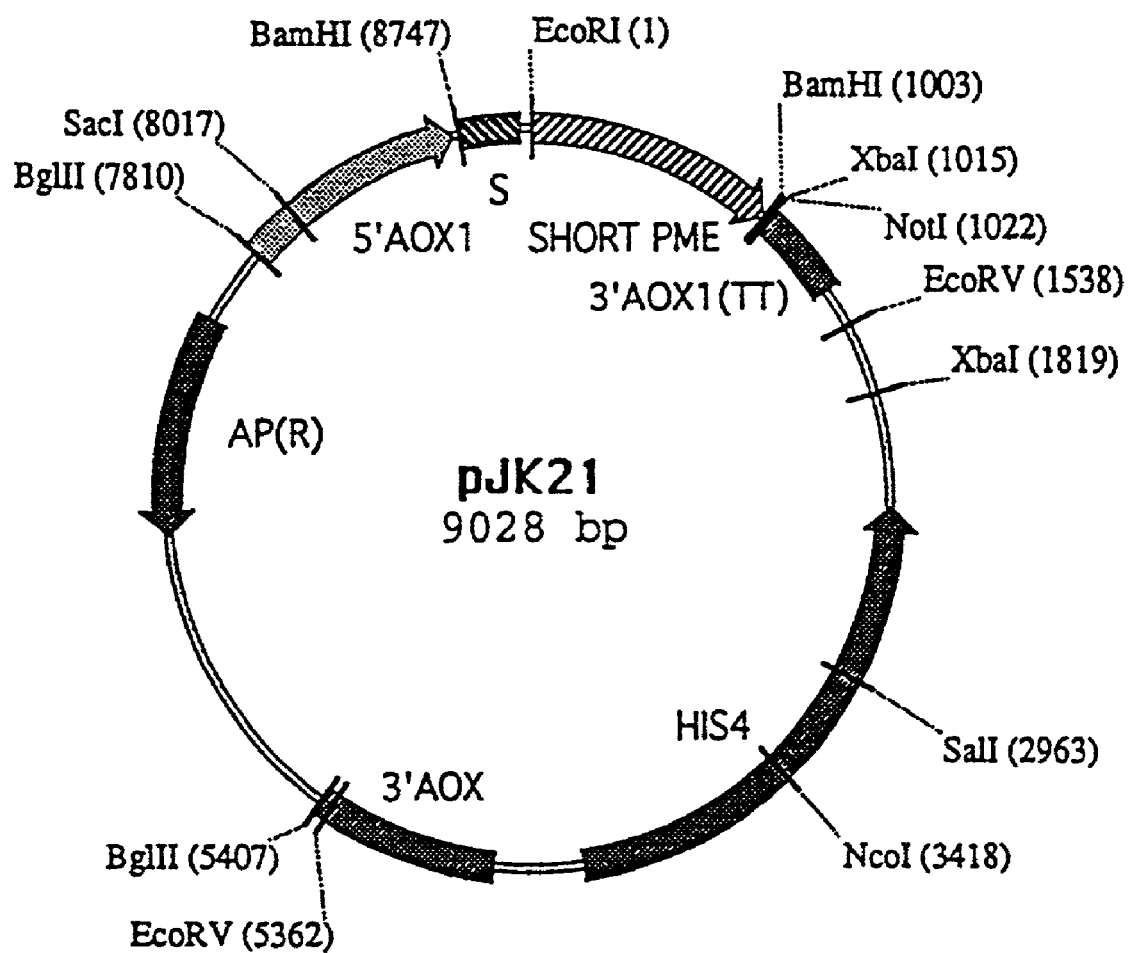

The present invention will now be described only by way of example, in which reference is made to the following attached Figures:

FIG. 1, which is a schematic diagram of a citrus fruit, such as an orange;

FIG. 2, which is a SDS PAGE gel of the recombinant enzyme of the present invention;

FIG. 3, which is a plot to determine pH optimum;

FIG. 4, which is a plot to determine temperature optimum;

FIG. 5, which is a plot to determine temperature stability;

FIG. 6, which is a plot to determine the $K_m$ value;

FIG. 7, which is a plot to determine activity in the presence or absence of NaCl;

FIG. 8, which is a plot to determine activity in the presence or absence of $Na_2SO_4$;

FIG. 9, which is a plot to determine activity in the presence or absence of $NaNO_3$;

FIG. 10, which is a plasmid map of pO17;

FIG. 11, which is a plasmid map of pO34;

FIG. 12, which is a diagrammatic representation of two genes;

FIG. 13, which is a plasmid map of pJK10;

FIG. 14, which is a plasmid map of pJK11;

FIG. 15, which is a plasmid map of pJK12;

FIG. 16, which is a plasmid map of pJK20;

FIG. 17, which is a plasmid map of pJK21; and

Figure 18:
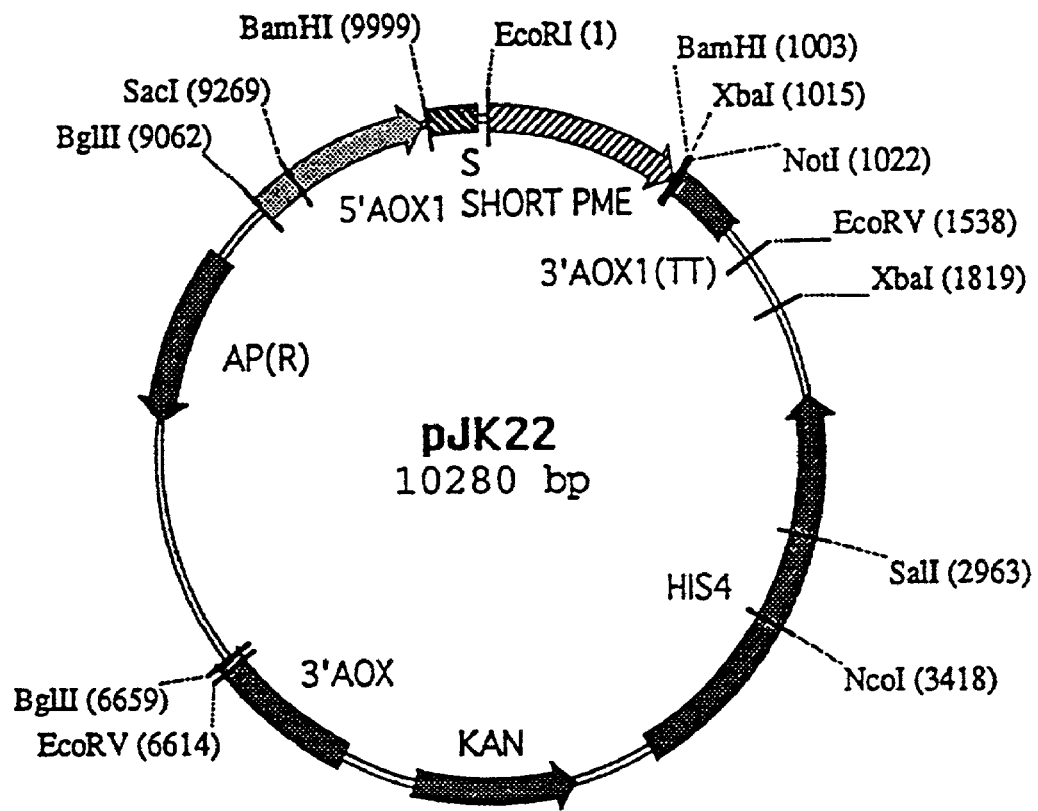

FIG. 18, which is a plasmid map of pJK22.

FIG. 1 was referred to in the above description. The other Figures are discussed in the commentary below.

EXPERIMENTAL SECTION

Materials and Methods for Biochemistry

Plant material: Immature Spanish oranges of the Navelina variety class I without seeds, were used for isolation of PME. The oranges were peeled manually and the peels were stored at −80° C.

Extraction of PME from Orange Peel

PME was purified according to the following procedure. All operations were performed at 4° C. 600 g frozen orange peels were thawed and cut into minor pieces. They were then homogenized in a Warring blender for 2 min in 1200 ml buffer (100 mM Na-succinate pH 6.2, 1 mM DTT). 36 g solid NaCl was added to the homogenate to reach an end-concentration of 3% (w/v) in order to isolate membrane bound proteins (Versteeg et al. (1978) Lebensmittel.-Wiss. u. Technol., 11: 267–274). After 2 hours incubation with gently stirring at 4° C. the suspension was filtered through nylon mesh and the filtrate was centrifuged at 10,000 rpm for 20 min to remove insoluble residues.

The supernatant was then fractionated using $(NH_4)_2SO_4$ precipitation. The supernatant was first precipitated with 30% $(NH_4)_2SO_4$ under slowly stirring for 30 min. After centrifugation at 20,000 rpm for 10 min the supernatant was further precipitated with 60% $(NH_4)_2SO_4$ for 30 min. The suspension was centrifuged as before and the precipitate was resuspended in 50 ml 50 mM MES, 1 mM DTT pH 6.8 and dialysed against the same buffer over night.

Chromatography

The dialysed sample was further separated by cation exchange chromatography. A 40–50 ml sample was applied to a CM-Sepharose™ CL-6B (1.5×15 cm) in two rounds with a 30 min wash between the rounds with buffer A: 50 mM MES, 1 mM DTT pH 6.8. After washing off the unbound proteins with buffer A the bound proteins were eluted with an increasing NaCl gradient from 0–0.4 M NaCl in total 500 ml. The flow was 25 ml/h and fractions of 8.33 ml were collected. The protein absorption profile was measured at 280 nm.

All fractions were analysed for PME activity and protein. The protein content was measured spectrophotometrically with the BioRad method.

The fractions containing PME activity were pooled and concentrated by press dialysis using Amicon filter system. Buffer exchange to 50 mM Tris, 1 mM DTT, 0.1 M NaCl pH 7 was done on the same system.

9 ml concentrated PME sample was then applied to a Sephacryl™ S-200 (2.6×70 cm) gel filtration column. The column was equilibrated with 50 mM Tris, 1 mM DTT, 0.1 M NaCl pH 7. The flow was 40 ml/h and fractions of 5.33 ml were collected. The fractions containing PME activity were pooled and concentrated.

Enzyme Activity

PME catalyses the cleavage of methylester groups from pectin. During the purification steps PME was detected by a fast method using methyl red indicator test. Due to cleavage of methyl groups from galacturonic acid residues in the pectin chain, carboxyl groups were formed and the pH drops in the assay. The pH indicator—methyl red—changes colour at pH drop from yellow (pH 6.2) to pink (pH 4.2). The assay contained 1 ml 0.5% Grindsted™ Pectin 1450 (DE 70%) (supplied by Danisco Ingredients, Danisco A/S) solubilized in 0.15 M NaCl pH 7 and 125 µl sample. The samples which showed positive methyl red test after 10 min incubation at 30° C. were then further measured by the titration method (Versteeg et al (1978) Lebensmittel.-Wiss. u. Technol., 11: 267–274).

With the titration method the assay contained 10 ml 0.5% lime pectin (Grindsted™ Pectin 1450—supplied by Danisco Ingredients, Danisco A/S) solubilized in 0.15 M NaCl pH 6.8 and 10–100 µl sample. Titration was performed with 0.02 M NaOH and the reaction was measured at room temperature. An automatic titrator was used (Versteeg et al. (1978) Lebensmittel.-Wiss. u. Technol., 11: 267–274).

SDS-PAGE/Western Blotting

The purity of the PME fraction was investigated by SDS-PAGE using Pharmacia PhastSystem™ with 10–15% SDS-gradient gels. Electrophoresis and silver staining of the proteins were done as described by the manuals from Pharmacia. For determination of pI IEF 3–9 PhastSystem™ gels were used.

Immuno gel electrophoresis was used for characterisation of polyclonal antibodies raised against orange peel PME. The enzyme fractions were separated on SDS-PAGE and transferred to NC-paper by semi-dry blotting technique on a Semidry transfer unit of the PhastSystem™. The NC-paper was incubated with the primer antibody diluted 1:50 and stained with the second antibody coupled to alkaline phosphatase (Dako A/S Glsotrup, Denmark) used in a dilution of 1:1000.

Peptide Mapping

PME was digested with either trypsin or endo-proteinase Lys-C from *Lysobacter enzymogenes* (both enzyme preparations were sequencing grade purchased from Boerhinger Mannheim, Germany).

100 µg purified PME was carboxy methylated with iodoacetamide to protect the reduced SH-groups. Then the protein was cleaved with trypsin (4 µg/20–100 µl). The hydrolytic cleavage was performed at 40° C. for 2×3 hrs. The reaction was stopped with addition of 20 µl TFA. After centrifugation at 15,000 rpm for 5 min the peptides were purified on a reverse-phase HPLC column (Vydac 10 C18 column). 2×500 µl samples were applied. The peptides were eluted and separated with an increasing acetonitrile gradient from 0.05–0.35% in 60 min in 0.1% TFA. The peptides were collected manually in Eppendorf tubes.

For digestion with endo-proteinase Lys-C, freeze dried PME (0.1 mg) was dissolved in 50 µl of 8 M urea. 0.4 M $NH_4HCO_3$, pH 8.4. After overlay with $N_2$ and addition of 5 µl of 45 mM DTT, the protein was denatured and reduced for 15 min at 50° C. under $N_2$. After cooling to room temperature, 5 µl of 100 mM iodoacetamide was added for the cysteines to be derivatised for 15 min at room temperature in the dark under $N_2$. Subsequently, 90 µl of water and 5 µg of endo-proteinase Lys-C in 50 µl 50 mM tricine and 10 mM EDTA, pH 8.0, was added and the digestion was carried out for 24 hrs at 37° C. under $N_2$.

The resulting peptides were separated as described for trypsin digested peptides.

Selected peptides were further purified on a Devosil 3 $C_{18}$ RP-HPLC column 0.46×10 cm (Novo Nordisk, Denmark). The purified peptides were then applied on an amino acid sequencer. Applied Biosystems 476A. using pulsed-liquid fast cycles.

Study 1

During purification of PME 600 g frozen orange peels were homogenized and after precipitation with 30–60% $(NH_4)_2SO_4$ and dialysis the sample was applied to a cation exchange column (CM-Sepharose™ CL-6B). PME binds strongly to a cation exchange column material at pH 6.8 whereas most of the proteins do not bind to the column and so elute in the wash volume. With increasing NaCl gradient PME eluted into two peaks with the major activity in PME I (fraction 49–53) at a NaCl concentration of 0.25 M. A minor PME peak eluted at a lower concentration of NaCl (fraction 25–32). The further purification was only performed for PME I, which contained the highest activity.

After concentration the PME fraction was further purified using gel filtration chromatography (Sephacryl™ S-200 column). Fractions containing the highest PME activity were pooled and concentrated on amicon filter dialysis.

In total approximately 4 mg PME was obtained from 600 g orange peels which corresponds to a protein yield of 12%.

SDS-PAGE showed only one protein band in the purified PME fraction with a MW of 36,000 D (FIG. 2). Isoelectric focusing of PME showed that the pI was >9.

Characterization and Kinetic Data

Characterization of PME and optima determinations were all done with the titration method as described in Materials and Methods.

pH optimum of PME activity was measured with 0.5% lime pectin (Grindsted™ Pectin 1450—supplied by Danisco Ingredients, Danisco A/S) in 0.15 M NaCl. The data are shown in FIG. 3. The optimum was found around pH 7–8.

Temperature optimum was found at 50° C.—see the data shown in FIG. 4.

The heat (temperature) stability of PME was determined by incubating the enzyme sample in Eppendorf tubes at different temperatures for 15 min. After incubation the enzyme activity was measured by traditional assay by the titration method. The stability of the enzyme activity was between 10°–40° C.—see the data in FIG. 5.

The affinity for lime pectin (Grindsted™ Pectin 1450—supplied by Danisco Ingredients, Danisco A/S) was determined by Lineweaver Burk plot of different pectin concentration versus activity. The data are shown in FIG. 6. The $K_m$ was calculated from the curve to be 0.07%.

We have also found that the PME could also de-esterify sugar beet pectin. Sugar beet pectin contains 60% galacturonic acid residues some of whose carboxyl groups are methylated (an approximate DE of 60%) and, in addition, some of the galacturonic acid groups are acetylated at C-2 and/or C-3. The PME activity was measured as described in Materials and Methods except that 1% sugar beet pectin solubilized in 0.15 M NaCl was used in the assay as the sugar beet pectin contained approx. 60% pectin. The results showed that the PME could de-esterify sugar beet pectin, even though the galacturonic acid residues are acetylated at the C-2C-3 positions.

|  | Enzyme activity (μmol/min/ml) |
|---|---|
| 0.5% lime pectin (Grindsted ™ Pectin 1450 - supplied by Danisco Ingredients, Danisco A/S) | 387 |
| 1.0% sugar beet pectin | 80 |

Further experiments showed that the PME of the present invention preferably requires NaCl for activity—see the data in FIG. 7. The activity increases with increasing NaCl concentration, with an optimum at 0.25 M NaCl. Higher concentrations are reducing the activity compared to the maximal activity.

Further experiments showed that other salts e.g. $Na_2SO_4$ or $NaNO_3$ can substitute NaCl for PME activity. The data are shown in FIGS. 8 and 9. The optimum activity was found at 0.2 M $NA_2SO_4$ and 0.3 M $NaNO_3$, respectively.

N-Terminal Analysis

Studies showed that the N-terminal sequence of native PME was blocked. De-blocking was achieved by treat PME blotted onto a PVDF membrane with anhydrous TFA for 4 min at 45° C. in tubes. After evaporation of most of TFA the tubes were placed at 65° C. for 4 hrs (Wellner, D. et al. (1990) Proc. Natl. Acad. Sci. 87: 1947–1949). The sequence obtained was SSSVTPNVVVAADSSGNFK and that N-acetylserine is the N-terminal residue of PME.

Immuno Histo Localization

For the preparation of tissue samples for immuno histo chemistry, thin slices of the middle part of mature fruit were fixed in 2% paraformaldehyde, 0.25% glutaraldehyde and 3% sucrose buffered with 0.05 M phosphate buffer pH 7. After incubation for 2 hours at 25° C. and 63 hours at 5° C. the specimens were washed 3×20 min in 0.05 M phosphate buffer pH 7. Dehydration was carried out using a series of ethanol washings (50%, 70%, 80% and 96%) followed by 3 washes of 99% ethanol (30 min for each ethanol concentration). After additional treatment with 2×2 hrs in petroleum (Shellsol™ D70k, Q7712) and 2×2 hrs in paraffin with 7% beeswax, the samples were embedded in paraffin. Cross-sections of 12.5 μm were made on a Supercut 2050 Reichart Jung pyramitome.

Immunology

Tissue sections were pre-incubated with 20% swine serum in TBS (0.5 M Tris/HCl pH 7.6, 0.15 M NaCl, 0.1% Triton X-100) for 30 min before treatment for 1 hour with PME antibodies were diluted 1:50 in TBS. Excess antibody was removed by washing with TBS for 5×5 min. After washing the sections were incubated for 30 min with secondary antibodies coupled with alkaline phosphatase 1:20 in TBS buffer. Surplus of secondary antibody was removed by TBS washing as described above. Before staining the sections were treated with veronal acetate buffer pH 9.2 for 5 min and then stained with Fast Red and Naphtol AS-BI phosphate (Sigma no N4875) for 20 min. Excess reagent was removed by washing with water. Controls were run in parallel and treated with pre-immune serum.

Results

Immunological localizations with the antibody raised against peel PME showed that PME is situated in large amounts in the outer cell layer of the lamella between the segments, in the core and in the outer cell layer of the juice sacs and also in the inner cell layer of the albedo (see FIG. 1). These results demonstrate that the antibody against peel PME cross reacts with PME from the flesh (the flesh consists of segments, see FIG. 1) indicating a high homology between the PME located in the peel and in the flesh, respectively.

Study 2

PME from orange peel was purified in large amounts. In this regard, approximately 70 mg PME was isolated from 5 kg orange peels. The purified PME was then used in the application test using milk protein—i.e. a drinking yoghurt. In this test, the block-wise enzymatically de-esterified pectin improved protein stabilising properties compared to non-de-esterified pectin, presumably because of the formed block structure. The final product also had a favourable viscosity.

Enzyme Isoforms

Whilst not wishing to be bound by theory, it is believed that the PME of the present invention can exist in at least two isoforms. Isoform S has a molecular weight of about 36 kD, and can be referred to as the "short PME". Isoform L has a molecular weight of about 64 Kd, and can be referred to as the "long PME".

It is also believed that the Isoform L is more heat stable than Isoform S. Also, it is believed that Isoform S starts the initial de-esterification step in a block-wise manner and is then superseded by Isoform L.

In other words, it is believed that Isoform L may have a greater affinity to partially de-esterified pectin than Isoform S.

It is believed that the heat stability of Isoform L may be due to the amino acid sequence represented as SEQ. I.D. No. 5.

Further studies have shown that the gene for Isoform L has an N-terminal extension upstream of the signal sequence. This is shown diagrammatically in FIG. 12.

Isolation and Characterization of cDNAS Encoding Pectin Methyl Esterase Obtainable from Orange Materials and Methods for Molecular Biology 1. Materials Oranges (*Citrus sinensis*) var. Navel originating from Morocco were used.

2. DNA

Genomic DNA was isolated as described by Dellaporta S. L. et al (1983) Plant Mol Biol Rep 1(4):19–21. Plasmid DNA was isolated as described in EP-B-0470145.

3. RNA

Total RNA was isolated from mature orange fruits. The outer portion of the flesh and the inner portion of the albedo layer (see FIG. 1) of a Navel orange fruit were used for the RNA isolation following the procedure described by Logemann J., Schell J. and Willmitzer L. (1987) Anal. Biochem 163:16–20. "Improved Method for the isolation of RNA from Plant Tissues".

4. PCR

Total orange RNA was used to make reverse PCR with the rTth Reverse PCR Kit (Perkin Elmer) according to the suppliers instructions with the following temperature cycling:

---

Reverse transcription:

70° C. 2 min
60° C. 2 min
50° C. 2 min
45° C. 5 min
40° C. 5 min
30° C. 10 min
42° C. 10 min
70° C. 2, 5 min
 5° C. soak Amplification (PCR):

94° C. 2 min
92° C. 1 min
45° C. 2 min
72° C. 2 min in 40 cycles
72° C. 5 min
 5° C. soak

---

5. Cloning Of PCR Fragments

PCR fragments were cloned into the EcoRV site of the vector pT7Blue (Novagen) following the suppliers instructions.

6. DNA Sequencing

Double stranded DNA was sequenced essentially according to the dideoxy method of Sanger et al. (1979) using the Auto Read Sequencing Kit (Pharmacia) and the Pharmacia LKB A. L. F. DNA sequencer (Ref: Sanger, F., Nicklen, S., and Coulson, A. R. (1979). DNA sequencing with chain-determinating inhibitors. Proc. Nat. Acad. Sci. USA 74: 5463–5467). The primers used for sequencing are listed below (presented 5' to 3'):

```
UNI (M13-20 Primer) - 17 Mer
GTAAACGACGGCCAGT

REV - 19 MER
GGAAACAGCTATGACCATG

01 - 20 MER
GACAACGGCAACGAGCCTCA

02 - 22 MER
GCACTTGTAATAACCCTAAAT

03 - 20 MER
CAGGGTAGTTTCCCGACGTA

04 - 20 MER
TACGTCGGGAAACTACCCTG

05 - 21 MER
CTCCTGGAAGCTTCATTGCTG

06 - 20 MER
GAAGCTTCTTGAAGAGAACG

07 - 20 MER
CGTTCTCTTCAAGAAGAAGCTTC
```

-continued

```
08 - 22MER
GAGGATAGCATGATGAGGCTCG

09 - 22 MER
GCAGTTCACAAAGAACTGGCGG

010 - 22 MER
CCTCATGATCATCATGTCAGTG

011 - 21 MER
GCTCCTCAGGGAGGCACTAAG

012 - 21 MER
CAGCAATGAAGCTTCCAGGAG

013 - 21 MER
CTTAGTGCCTCCCTGAGGAGC

014 - 18 MER
GCCACCGCCTGGTGCTTT

015 - 18 MER
AAAGCACCAGGCGGTGGC 016-20 MER
GCGGGATGCGTTGTCAGACG 017-20 MER
GAGGCACTAAGCGGTATT

018 - 18 MER
GCAACTGTAGCAGACTTG

019 - 20 MER
CACTGACATGATGATCATGA 020-20 MER
CAATTAAGCAGTTCACAAAG

021 -20 MER
AATATACCGCTTAGTGCCTC
```

The sequenced nucleotide sequence is shown as SEQ. I.D. No. 3 (derived from pO17) and SEQ. I.D. No. 4 (derived from pO34). The N-terminal sequence is shown as SEQ. I.D. No. 6.

7. Screening Of The Library

A cDNA library in lambda zapII (Stratagene) which had been prepared from mRNA isolated the flesh and albedo layer of the orange fruit was screened with the appropriate radio labelled PCR probe. The screening was performed according to the suppliers instructions except that the pre-hybridization and hybridization was performed in 2×SSC. 0.1% SDS, 10× Denhardt's and 100 µg/ml denatured salmon sperm DNA. Hybridization was overnight at 67° C. The filters were washed twice in 2×SSC. 0.1% SDS, twice in 1×SSC, 0.1% SDS and twice in 0.1×SSC, 0.1% SDS.

8. Probe

The cloned PCR fragment was isolated from the pT7 blue vector by digestion with the appropriate restriction enzymes. The fragment was separated from the vector by agarose gel electrophoresis and the fragment purified and radiolabelled using the Ready to Go™ DNA labelling kit (Pharmacia).

9. Southern Analysis

Genomic orange DNA or plasmid DNA were digested with appropriate restriction enzymes, transferred to HybondN+™ membranes and hybridized following the suppliers (Amersham) instructions.

10. In situ Hybridization Experiments

In situ hybridization technique is based upon the principle of hybridization of an antisense ribonucleotide sequence to the mRNA. The technique is used to visualize areas in microscopic sections where said mRNA is present. In this particular case the technique was used to localize the mRNA encoding the enzyme pectin methyl esterase in sections of *C. sinensis*.

Preparation of Tissue Samples for in situ Hybridization.

Thin slices of the middle part of a mature orange fruit were fixed by fixation with FAA fixation (45% ethanol, 5% formalin (40% paraformaldehyde) and 5% acetic acid) and incubation for 2 h at 25° C. and 63 h at 5° C. The samples were washed for 3×20 min in a 0.05 M phosphate buffer, pH 7. Dehydration was carried out using a series of ethanol washes (50%, 70%, 80%, 96%) ending with 3 washes in 99% ethanol. Each wash was for 30 min. The samples were then treated with petroleum (Shellsol™ D70k, Q7712) in 2×2 h and for another 2×2 h in paraffin with 7% beeswax. After this the samples were embedded in paraffin. Cross-sections of 12.5 µm were made using a Supercut 2050 Reichart Jung pyramitome.

Preparation of $^{35}$S Labelled Probes for in situ Hybridization

A 501 bp PCR fragment from a second PCR amplification was cloned into the pT7blue vector (Novagen) in both directions. The pT7 vector contains a T7 promoter. The transcription of the antisense RNA and the sense RNA were driven by the SP7 promoter after digesting the plasmids with BamHI. A Maxiscript Kit™ (Ambion) was used with the following modifications. The transcripts were mn on a 6% sequencing gel to remove the incorporated nucleotide and eluted with the elution buffer supplied with the T7 RNA polymerase in vitro transcription kit (Ambion). The transcripts contained 55 non-coding nucleotides at one end and also 9 non-coding nucleotides at the other end. For hybridization $10^7$ cpm/ml of the $^{35}$S labelled probe was used.

In situ hybridization was performed essentially as described by Langedale J. A.(1994) in the Maize Handbook-M. Freeling and V. Walbot, eds. pp 165–180 Springer-Verlag, New York, Inc. The hybridization temperature was found to be optimal at 57° C. After washing at 57° C. the sections were covered with Kodak K-5 photographic emulsion and left for 3 days at 5° C. in the dark.

11. Results

The following sequence information was used to generate primers for the PCR reactions mentioned below and to check the amino acid sequence generated by the respective nucleotide sequences—see attached SEQ. I.D. No.s 7–19.

Peptide Sequences of Pectin Methyl Esterase Used for Generation of Primers

The Amino Acid Sequence (PE701,7–13) Used to Generate Primer B (Glu Ala Gln Ala Phe Thr Pro)

Primer B

GT(AG)AA(GATC)GC(TC)TG(GATC)GC(TC)TC 128 mix (the sequence corresponds to the complementary strand)

Generation of PCR DNA Fragment Partially Encoding Pectin Methyl Esterase

The amino acid sequences of the two non-overlapping peptides (described above) were used to generate mixed oligonucleotides. These were used as primers for reverse transcription and the following amplification (PCR) of total RNA. The resulting PCR clone was sequenced and had an insert of 501 bp. The deduced amino acid sequence from the nucleotide sequence corresponded nearly perfectly with the peptide sequences given in SEQ. I.D. No.s 7–19.

In situ Hybridization Analysis

The in situ hybridization experiments (see Materials and Methods) with the riboprobes (produced from the appropriate PCR clones) against the mRNA of pectin methyl esterase, showed strong hybridization in the outer cell layer of the lamella between the segments (see FIG. 1). Strong signals were also obtained from the outer cell layer of the juice sacs, the inner cell layer of the albedo and the core. These results correspond very well with the immunological localizations results seen with the antibody raised against peel PME as described previously.

Southern Analysis

Southern analysis showed that additional copies of the isolated PME genes (represented by the cDNA clones) are present in the *C. sinensis* genome. These other PME genes were rather homologous with the ones represented in pO17 and pO34.

In this regard, we observed in each lane one band of a strong hybridization signal, two bands of a middle hybridization signal and at least two more bands of a weaker signal compared with the rest. This pattern indicates that *C. sinensis* has at least between 5 and 7 copies of PME genes in the genome.

Isolation and Characterization of Novel PME cDNAs

A cDNA library in lambda zapII (Stratagene) which had been prepared as described in Materials and Methods was screened with the radiolabelled 501 bp insert from the PCR clone. Several hybridizing clones were identified and plasmid DNA was excised in vivo according to the suppliers instructions. The size of the cDNA inserts in the clones were determined by digestion with EcoRV and SmaI followed by agarose gel electrophoresis. One clone pO34 had an insert size of approximately 2 kb whereas another clone pO17 had an insert size of approximately 1.4 kb. These clones were

```
Asn Cys Asp Met Leu Ala Tyr Gln Asp Thr Leu Tyr                              (PE492B)

Val ILe Thr Ser Ala Thr Glu Ala Gln Ala Phe Thr Pro Gly Ser Phe Ile Ala Gly Ser   (PE701)

Ser Trp Leu Gly Ser Thr Gly Phe
```

The Amino Acid Sequence (PE492B,4–7) used to Generate Primer A (Met Leu Ala Tyr Gln Asp Thr)

Primer A

ATG(CI)T(GATC)GC(GATC)TA(TC)CA(AG)GA(TC) AC 256 mix selected for further analysis. The nucleotide sequences were determined and are shown as SEQ. I.D. NO. 3 and SEQ. I.D. No. 4 for pO17 and pO34, respectively.

The open reading frame in 034 starting at nucleotide 29 and ending at nucleotide 1780 encodes a PME of 584 amino acids including a putative signal peptide. A possible cleavage site between glycine at position 46 and isoleucine at position 47 can be predicted according to the rules of von Heijne, G.(1986) Nucl Acids Res 14, 4683–4690 "A new method for predicting signal sequence cleavage sites", thereby giving a long mature PME enzyme of 538 amino acids having a calculated molecular weight of 58386 dalton. The molecular weight of the long PME including the signal sequence can be calculated to 63502 dalton. pO34 nucleotide sequence includes an untranslated 5' region of 29 nucleotides and a untranslated 3' region of 186 nucleotides, ending in a poly A tail.

The open reading frame in O17 starts at nucleotide 18 and terminates at nucleotide 1103. It encodes a short PME of 362 amino acids including a signal peptide of 44 amino acids. A putative cleavage site can be predicted between glutamine at position 44 and the serine at position 45 leaving a mature short PME starting with the amino acid sequence Ser-Ser-Ser-Val-Thr-Pro. This N-terminal amino acid sequence is identical to the N-terminal amino acid sequencing of the purified short type of PME as described in the biochemical section. The amino acids sequences obtained from the purified enzyme were aligned with the deduced mature amino acid sequence of pO17. Full identity was found for the peptide fragments.

There was nearly full identity between all the sequenced peptides and the deduced amino acid sequence in pO17 and also with the amino acid sequence deduced from pO34. the long PME. In this regard, pO17 differs at one amino acid position (no. 24 in the sequence encoding the mature polypeptide). The mature short PME protein has a calculated molecular weight of 33954 dalton. The calculated molecular weight of the short PME form including the signal peptide is 39088 dalton. O17 includes a 5' untranslated region of 17 nucleotides and a 3' untranslated region of 180 nucleotides, ending in a polyA tail.

The major difference between the long and the short PME enzyme is an N-terminal extension of 220 amino acids present in the mature enzyme derived from O34 and presented as SEQ. I.D. No. 5. The corresponding nucleotide sequence encoding this region of the long PME enzyme is shown as SEQ. I.D. No. 6.

Expression of PME in Micro-Organisms

The DNA sequence encoding either the long or the short form of orange PME was introduced into micro-organisms to produce a recombinant enzyme in large quantities having a high specific activity to be used for enzymatic treatment of pectin.

Expression in *Pichia pastoris*

Construction of pJK10, pJK11 and pJK12 (see FIGS. 13–15)

pO34 plasmid DNA was used as template DNA in a PCR reaction with the following set of primers:

5'-GAATTCATTGTCGCCGGAGTGAAC-3' with an EcoRI site at one end and

5'-AAGACCAGAGACCTATGGATCCAC-3' with a BamHI site near the end.

Combining AmpliTaq$^R$ DNA Polymerase (Perkin Elmer), template DNA, dATP, dGTP, dCTP and dTtP and the two primers in the following buffer:

60 mM Tris-HCl (pH 8.5), 15 mM (NH$_4$)$_2$SO$_4$ and 1.5 mM MgCl and using the following temperature cycle:

94° C. 2 min
94° C. 1 min
55° C. 2 min
72° C. 2 min in 35 cycles
72° C. in 7 min
5° C. soak produced the expected PCR product of 1690 bp which was purified and subcloned into the vector pT7Blue (from Novagen) following the suppliers instructions.

Resulting clones (called pT7-O34) containing an EcoRI-BamHI fragment of the expected size were further verified by DNA sequencing (see Materials and Methods for Molecular Biology). A pT7-O34 subclone containing the correct sequence was digested with EcoM and BamHI and the fragment of 1685 bp was purified and subcloned into the *Pichia pastoris* vector pHIL-S1 (from Invitrogen) digested with the same enzymes.

The sequence encoding the mature long form of PME was cloned in this way in frame with the PHO1 secretion signal (S) in the vector. The resulting plasmid is called pJK10 and is shown in FIG. 13.

To create pJK11 (see FIG. 14) the EcoRI-BamHI fragment of the pT7-O34 clone was further subcloned into a pBSK-vector (from Stratagene) digested with the same enzymes. Then, an EcoRI-NotI fragment from one of the resulting clones (verified by DNA sequencing) was subcloned into the *Pichia pastoris* expressions vector pPIC9 (from Invitrogen) digested with the same enzymes. This places the reading frame encoding the mature protein, of the long form of PME, downstream and in frame with the alpha-factor secretion signal (S) in pPIC9, see FIG. 14.

In addition, the EcoRI-NorI fragment from pT7-O34 was also subcloned into the pPIC9K (Invitrogen) vector creating the pJK12 plasmid shown in FIG. 15. The only difference between pJK11 and pJK12 is a gene encoding resistance for kanamycin and this is situated in pJK12.

Both the PHO1 secretion signal in pJK10 and the alpha secretion signal in pJK11 and pJK12 can direct the secretion of the mature polypeptide encoding the long form of PME.

Construction of pJK20, pJK21 and pJK22 pO17 plasmid DNA was used as a template DNA in a PCR reaction with the following primers:

5'-GAATTCTCCTCGTCGGTGACACCG-3' with an EcoRI site at one end and

5'-AAGACCAGAGACCTATGGATCCAC-3' with a BamHI site near the end.

The template DNA, AmpliTaq$^R$ polymerase, dATP, dGTP, dCTP and dTTP were combined with the buffer (60 mM Tris-HCl, pH 8.5; 15 mM (NH$_4$)$_2$SO$_4$ and 1.5 mM MgCl$_2$) and placed in a thermoblok with the following temperature cycle:

94° C. 2 min
94° C. 1 min
55° C. 2 min
72° C. 2 min in 35 cycles
72° C. in 7 min
5° C. soak This produced an expected PCR band of 1008 bp which was purified and subcloned into pT7Blue (Novagen). The resulting clones were verified by DNA sequencing as explained above. A plasmid with the correct sequence was digested with EcoRI and BamHI and the resulting fragment further subcloned into the pHIL-S1 vector (Invitrogen) the resulting plasmid is called pJK20 (shown in FIG. 16) and in this, is the region encoding the mature polypeptide of the short form of PME situated in frame and downstream of the PHO1 secrection signal.

Plasmid pJK21 and pJK22 were constructed in the same manner as explained for the pJK11 and pJK12 except that the EcoRI-NotI fragment was obtained from the pBSK-O17 clone. FIGS. 17 and 18 show the resulting plasmids where the region encoding the mature polypeptide is situated downstream, and in frame, of the alpha secretion signal in respectively pPIC9 and pPIC9K.

Introduction of the Long or the Short Form of PME into *Pichia pastoris* by Spheroplast Formation and Transformation The plasmids pJK10, pJK11, pJK12, pJK20, pJK21 and pJK22 were introduced in separate experiments into *Pichia pastoris* GS115 cells.

In this regard, spheroplasts were prepared from the GS115 cells growing in yeast extract peptone dextrose medium (YPD) at 28–30° C. The preparation of spheroplasts and the transformation procedure were performed as described in the *Pichia* expression kit: Instruction Manual (Invitrogen). The resulting *Pichia pastoris* Mut$^+$ or Mut$^s$ transformants were then analyzed for the expression of the recombinant PME gene by assaying the supernatant for PME activity using the methods described in: Materials and Methods for Biochemistry.

Screening of Transformants for High Expression of the Long or the Short Form of PME Putative positive transformants were further grown in minimal medium (either Minimal Dextrose Medium or Minimal Glycerol Medium as specified in the Pichia expression kits Instruction Manual, Invitrogen) and the genomic DNA was isolated and analysed by PCR as described in the Instruction Manual.

Positive clones found in the initial screen, which also produced a PCR band of the expected size, were selected and further grown in a flask at 28–30° C. following the procedure described in the *Pichia* Instruction Manual.

At least 10 verified recombinant clones of each construct (pJK10, pJK11, pJK12, pJK20, pJK21 and pJK21) were screened for secretion of PME and their relative expression level were measured over time by sampling every 2 to 6 hours. The cells in the samples were pelleted and the supernatant assayet for PME activity following the methods explained in: Materials and Methods for Biochemistry.

The clones obtained after transformation with either pJK12 or pJK22 were preselected using the integrated Kanamycin resistance gene as the selector gene as described by Scorer C. A. et al.(1994) Bio/Technology vol 12, pp181–184 and Laroche Y. et al (1994) Bio/Technology vol 12, pp 1 119–1124. In this way multiple copy integration transformants were obtained and further screened as described above.

Transformants representing either the long or the short form of PME and shown to express the recombinant protein in high levels were selected and further analyzed by Western Blot analysis (see Materials and Methods for Biochemistry).

Purification and Charaterization of Recombinant PME

Recombinant PME protein was purified from the cultures supernatant using the procedures described in the Materials and Methods for Biochemistry as necessary.

The presumed high temperature stability of the long form of PME was verified by testing the enzyme activity after incubation at different temperatures as explained in the section: Charaterization and kinetic data. The purified recombinant enzymes (both the long and the short PME form) were further characterized as explained in the: Characterization and kinetic data section. These analyses showed that both types had a pH optimum around 7–8 and the temperature stability of the short recombinant PME was found to be between 10 and 40° C. and up to 80° C. for the long recombinant PME.

Expression in *Aspergillus niger*

In another embodiment, pO34 or pO17 was digested with the appropriate restriction enzymes and the coding sequence for the long or the short form of PME of the present invention was cloned into the *Aspergillus* expression vector pBAMTE1 (containing methyl tryptophan resistance promoter from *Neurospora crassa*) for expression in *Aspergillus niger* (Pall et al. (1993) Fungal Genet Newslett, vol 40 pp 59–62).

The protoplasts were prepared according to Daboussi et al. (Curr Genet (1989) vol 15. pp453–456) using lysing enzymes Sigma L-2773 and the lyticase Sigma L-8012. Transformation of the protoplasts followed the protocol stated by Buxton et al. (Gene (1985) vol 37 pp 207–214) except that for plating the transformed protoplasts the protocol laid out in Punt et al. (Methods in Enzymology (1992) vol 216 pp447–457) was followed but with the use of 0.6% osmotic stabilised top agarose.

The results showed that purified orange PME activity was obtainable from *Aspergillus niger* cultures.

Uses

Effect of Orange PME Treated Pectin on the Viscosity and Stability of Protein Drinks Methods Enzymatic Treatment of Pectin with PME Derivable from Orange A batch of enzymatically treated pectin was prepared as follows:

125 g pectin was dissolved in hot water under efficient stirring. 45.3 g NaCl (reagent grade) was added and the volume adjusted to 4.0 l with water. This solution was stirred until the salt had dissolved. The pectin solution was cooled to 40° C. and the pH was increased to pH 7.0, using 1 N NaOH (reagent grade) and efficient stirring. An appropriate sample of orange PME was added and the enzymatic reaction continued until the desired degree of esterification was achieved. The pH was kept constant at pH 7 by automatic dosage of 1 N NaOH (reagent grade) during the incubation period, and the enzymatic reaction was followed by the consumption of NaOH.

When the pectin sample had reached the desired degree of de-esterification the NaOH addition was stopped, the pH of the solution lowered to about 3.0 by addition of 2% HCl. The pectin solution was then heated to 70° C. for 5 min to completely inactivate the enzyme. The treated pectin was precipitated with 1 volume of isopropanol, washed with 60% isopropanol and pressed to about 50% dry matter. The enzymated pectin batch was then air dried at 40° C. and finally milled to a dry powder.

Protocol

Determination of Pectin Samples for Calcium Sensitivity Index (CF)

Calcium sensitivity is measured as the viscosity of a pectin dissolved in a solution with 57.6 mg calcium/g pectin divided by the viscosity of exactly the same amount of pectin in solution, but without added calcium. A non calcium sensitive pectin has a CF value of 1.

4.2 g pectin sample is dissolved in 550 ml hot water with efficient stirring. The solution is cooled to about 20° C. and the pH adjusted to 1.5 with 1N HCl. The pectin solution is adjusted to 700 ml with water and stirred. 145 g of this solution is measured individually into 4 viscosity glasses. 10 ml water is added to two of the glasses (double determinations) and 10 ml of a 250 mM $CaCl_2$ solution is added to the other two glasses under stirring.

50 ml of an acetate buffer (0.5 M, pH about 4.6) is added to all four viscosity glasses under efficient magnetic stirring, thereby bringing the pH of the pectin solution up over pH 4.0. The magnets are removed and the glasses left overnight at 20° C. The viscosities are measured the next day with a Brookfield viscometer. The calcium sensitivity index is calculated as follows:

$$CF = \frac{\text{Viscosity of a solution with 57.6 mg Ca}^{2+}/\text{g pectin}}{\text{Viscosity of a solution with 0.0 mg Ca}^{2+}/\text{g pectin}}$$

Determination of Pectin Samples Degree of Esterification (% DE)

To 50 ml of a 60% isopropanol and a 5% HCl solution is added 2.5 g pectin sample and stirred for 10 min. The pectin solution is filtered through a glass filter and washed with 15 ml 60% isopropanol/5% HCl solution 6 times followed by further washes with 60% isopropanol until the filtrate is free of chlorides. The filtrate is dried overnight at 80° C.

20.0 ml 0.5 N NaOH and 20.0 ml 0.5 N HCl is combined in a conical flask and 2 drops of phenolphtalein is added. This is titrated with 0.1 N NaOH until a permanent colour change is obtained. The 0.5 N HCl should be slightly stronger than the 0.5N NaOH. The added volume of 0.1 N NaOH is noted as $V_0$.

0.5 g of the dried pectin sample (the filtrate) is measured into a conical flask and the sample is moistened with 96% ethanol. 100 ml of recently boiled and cooled destined water is added and the resulting solution stirred until the pectin is completely dissolved. Then 5 drops of phenolphtalein are added and the solution titrated with 0.1 N NaOH (until a change in colour and pH is 8.5). The amount of 0.1 N NaOH used here is noted as $V_1$. 20.0 ml of 0.5 N NaOH is added and the flask shaken vigorously, and then allowed to stand for 15 min. 20.0 ml of 0.5 N HCl is added and the flask is shaken until the pink colour disappears. 3 drops of phenolphtalein are then added and then the resultant solution is titrated with 0.1 N NaOH. The volume 0.1 N NaOH used is noted as $V_2$.

The degree of esterification (% DE: % of total carboxy groups) is calculated as follows:

$$\% DE = \frac{V_2 - V_0}{V_1 + (V_2 - V_0)}$$

Yoghurt Production

Standardised skimmed milk (prepared by mixing powdered milk with an adequate volume of water) was heated at 90° C. in 5 min and then homogenized at 200 kp/cm² and the milk cooled to 31° C. Yoghurt culture was added and the milk fermented to about pH 4.0. The yoghurt was cooled to about 20° C. and the pectin sample was added as a saturated sugar solution (about 65% sugar) and stirred for 15 min. The pH was adjusted t6 pH 4.0 with lactic acid. The yoghurt was pasteurized at 88° C. for 15 seconds and homogenized at 150 k/cm², then cooled to 20° C. and filled into sterile 250 ml blue cap bottles (200 ml/bottle).

The composition of the final product was: 7.6% MSNF (milk solid content), 9.15% sugar and 0.25% or 0.35% pectin sample giving total solids of 17.0% or 17.10%, respectively.

Viscosity Determination of Yoghurt Drink

The viscosity of a yoghurt sample was determined (double determinations) using either a Bohlin Rheomete™ (supplied by Bohlin Instruments) with shear rates 18.5–46.0 or a using a StressTech™ (Rheologica instruments AB) with the same shear rates.

Protein stability Measured by z Centrifugation Test 20 g of a sample (e.g. drinking yoghurt) is centrifuged at 10° C., 2300× g for 20 min. The supernatant is discarded and the centrifuge glass placed upside down for 30 min. The glass is weighed and the % sedimentation was calculated as follows:

$$\% \text{ Sedimentation} = \frac{\text{Wgt of glass after centri} - \text{Wgt of glass}}{\text{Wgt of sample}} \times 100$$

Where Wgt=weight and centri=centrifugation

Protein Stability as Judged by Particle Size Distribution in the Sample

Particle size distribution of a yoghurt sample was determined by the use of a Malvern 2600 Easy™ sizer. The particle size is determined by laser light scattering by this method. 1 ml yoghurt sample was added to 9 ml de-areated buffer solution (30.7% 0.1 M citric acid, 19.3% 0.2 M $Na_2HPO_4$ and 50.0% water) and mixed. The de-areated buffer is added to the measuring glass and the mixture of sample/buffer is added droplet by droplet until the optimum concentration is obtained. The average particle size is calculated from the measurements.

A yoghurt with the average particle size below about 3 μm is considered rather stabile while a yoghurt with an average particle size over about 10 μm and higher is considered not to be stabile for long term storage.

Determination of Long-Term Stability

Samples were stored at 4° C. or at ambient temperature and the whey separation was measured (in mm of whey at the top of the sample, in the bottle). The sample was filled in 250 ml blue cap bottles (double determinations). The depth of the sample in each case was approximately 70 mm—which corresponded to the 200 ml mark for each bottle.

EXAMPLE 1

Sour Milk Drink

The purpose of adding pectin to a sour milk drink (e.g. a yoghurt drink) is to produce a drink that remains physically homogenous during the bacteriological and organoleptic shelf life of the drink. In addition the treatment of the yoghurt drink for long term storage destabilizes the protein in the drink giving rise to a drink with a sandy mouthfeel and showing rather quickly syneresis, if pectin is not added.

Treatment of the Pectin

A commercially available high ester pectin; Grindsted™ Pectin URS (Ultra Rapid Set pectin type) was chosen as the mother pectin, due to its high ester level (% DE of 82, see FIG. 19). The treatment with the orange PME enzyme of this mother pectin is explained in the method section.

The enzymatic reaction was stopped and the resulting experimental pectin (called pectin no 1944–96–2) was investigated for its degree of esterification, by the method described in the method section. In addition, to compare the two pectin types, the mother pectin and the treated pectin, with a known good commercial drinking yoghurt pectin type, the Grindsted™ Pectin AM453 was included in the experiments.

The relative calcium sensitivity of the three chosen pectins was determined as explained in the method section: Determination of pectin samples calcium sensitivity index (CF), and the results are shown in the Table below.

| Pectin-type | Δ CF | DE % |
| --- | --- | --- |
| Grindsted ™ Pectin URS | 1.1 | 82 |
| Pectin 1944-96-2 | 1.4 | 76 |
| Grindsted ™ Pectin AM453 | >20 | 72 |

De-esterification of the Grindsted™ Pectin URS mother pectin from 82% DE down to 76% DE gave nearly no change in the calcium sensitivity of the these two pectins (a Δ CF of 1 have no sensitivity). A pectin with measurable calcium sensitivity could be produced by further treatment with the orange PME enzyme on the mother pectin down to 70% DE, since this pectin had a Δ CF of 14.

Results of Yoghurt/Drinking Yoghurt Analysis

Yoghurt was produced as explained in the method section. The three pectins (Grindsted™ Pectin URS, Pectin 1944–96–2 and Grindsted™ Pectin AM453) were used individually in the following recipes:

7.6% MSNF (milk solid content), 9.15% sugar and 0.25% or 0.35% pectin sample giving total solids of 17.0% or 17.10%, respectively in the final product.

The quality of the individual yoghurt produced was investigated by their sedimentation % seen in the centrifugation test, by measuring the particle size in the yoghurt, by measuring the viscosity and by examination of possible whey separation during long time storage, as described in the method section.

The sedimentation of the yoghurt produced with the three pectin types are presented in the Table below.

| SEDIMENT (IN %) OF THE YOGHURT | | |
| --- | --- | --- |
| Pectin-type | Concentration - 0.25% | Concentration - 0.35% |
| Grindsted ™ Pectin URS | 29.40 | 21.02 |
| Pectin 1944-96-2 | 1.53 | 2.95 |
| Grindsted ™ Pectin AM453 | 2.20 | 1.85 |

The results are the average of from one to four individual production.

It is clear that the mother pectin (URS type) had a high sedimentation % and consequently the yoghurt produced showed whey separation and was unstable at both pectin concentrations used (0.25 and 0.35%). This is not surprising since normally the URS pectin type cannot be used for stabilization of heat treated yoghurt types for long time storage.

The yoghurt produced with the Pectin 1944–96–2 showed stability at both pectin dosages used and low sedimentation as seen by the above results, and no whey separation after over 75 days of storage. In comparison, the excellent Grindsted™ Pectin AM453 normally used in yoghurt production also showed low sedimentation, as expected, and produced stabile yoghurts with no whey separation (see results above).

By treating the mother URS pectin with orange PME an unsuitable pectin was made suitable as a stabilizing agent in the yoghurt, and this treated pectin behave just as well as an excellent commercial stabilizer.

Further examination of the produced yoghurts by particle size determination (see the methods section) were performed and the results are shown in the Table below.

| PARTICLE SIZE (IN μM) OF THE YOGHURT | | |
| --- | --- | --- |
| Pectin-type | Concentration - 0.25% | Concentration - 0.35% |
| Grindsted ™ Pectin URS | 9.32 | 6.41 |
| Pectin 1944-96-2 | 1.33 | 1.55 |
| Grindsted ™ Pectin AM453 | 1.40 | 1.53 |

The average particle size (the number corresponding to the D(4.3)) fraction using the Malvern instrument, is shown) of the yoghurt produced with the mother URS pectin is high, as expected. Again the results are an average of one to four productions.

The average particle size of the yoghurt produced from both the pectin 1944-96-2 and the Grindsted™ Pectin AM453 are small at both pectin dosages used (see results above). Again showing that the yoghurt produced with these pectin types are suitable to produce stabile yoghurts.

Finally, and very importantly, in the case of drinking yoghurt production for long time storage, the viscosity was determined and the results are shown in the Table below.

| VISCOSITY (IN MPa s) OF THE YOGHURT | | |
| --- | --- | --- |
| Concentration/Pectin- type | Concentration - 0.25% | Concentration - 0.35% |
| Grindsted ™ Pectin URS | 55 | 40 |
| Pectin 1944-96-2 | 12 | 18 |

-continued

VISCOSITY (IN MPa s) OF THE YOGHURT

| Concentration/ Pectin- type | Concentration - 0.25% | Concentration - 0.35% |
| --- | --- | --- |
| Grindsted ™ Pectin AM453 | 24 | 43 |

Since the mother URS pectin could not stabilize the yoghurt the viscosity obtained is, as expected rather high at both pectin concentrations. The excellent Grindsted™ Pectin AM453 which produced stabile yoghurts with low sedimentation and low particle size showed a viscosity of about half the viscosity seen with the Grindsted™ Pectin URS pectin at the 0.25% pectin dosage and approximately the same as the URS pectin at the 0.35% pectin dosage—irrespective of the fact that only the AM453 pectin produced a stabile yoghurt.

In both the URS and the AM453 cases the higher viscosity seen could partly be attributed to the amount of pectin added, especially this seems to be the situation in the AM453 pectin case since an increase in the amount of pectin added (from 0.25 to 0.35%) produced nearly twice as viscous a yoghurt.

The viscosity obtained with the orange treated PME pectin 1944-96-2 shows a dramatic fall in viscosity compared with the mother URS pectin at 0.25% concentration. This is partly due to the stabilization of the yoghurt with the 1944-96-2 pectin but not the only reason since the AM453 yoghurt has twice as high a viscosity at that pectin dosage. Indeed, adding 0.35% of the 1944-96-2 pectin to the yoghurt only increases the viscosity with 6 units (compared with the 0.25% dosage) while the viscosity increases with 19 units going from 0.25% to 0.35% in the AM453 case.

The orange PME treated pectin 1944-96-2 can stabilize yoghurt having a very low viscosity, despite the pectin dosage was 0.25% (or 0.35%), which gave nearly twice as high a viscosity using other untreated pectins—e.g. Grindsted™ Pectin AM453.

This is a new and very important development for the production of sour milk drinks.

By treating the Grindsted™ Pectin URS with orange PME a new pectin type is created which in contrast to the mother pectin can stabilize yoghurt and most importantly shows much lower viscosity than normally used pectins. Other high ester pectin can also be improved by treatment with the orange PME.

EXAMPLE 2

Whey Juice Drink

The modified pectin according to the present invention (as prepared above) was used in a whey juice drink as follows:

| Sweet or acid whey | 42.00% |
| --- | --- |
| Fruit juice | 40.00% |
| Sugar | 8.00% |
| Sodium citrate | 0.20% |
| PME modified pectin | 0.20% |
| Grindsted Flavouring | + |
| Water | 9.60% |

Dry PME modified pectin, sodium citrate and sugar were mixed and then dissolved in water at 80° C. This pectin solution was cooled to below 5° C. and whey was added at 5° C. Grindsted Flavouring (supplied by Danisco Ingredients, Danisco A/S) and juice were added slowly and the pH in the sample mixture was adjusted with citric or lactic acid to pH 4.0. The sample mixture was aged for approx. 30 min under agitation. The pasteurisation was performed at 80° C./15 seconds and homogenisation at 200 bar (2900 psi). The samples were cooled to 20° C. and filled aseptically in containers.

Sample tests were analysed after 24 hours, 1 months and 6 months incubation at room temperature. The investigation analysis included viscosity measurements, stability index particle size and long-term stability—the protocols for which are described above.

The results showed improved stability and a long-term stability in the whey juice drink processed with PME modified pectin compared to the reference pectin employed in the control tests. In addition, the whey juice drink had a favourable viscosity which was lower than the control drinks.

The whey juice drink was also processed with plant PME modified lime and lemon pectin, respectively,—i.e. modified with the PME of the present invention. The results demonstrate that PME modified pectin has improved protein stability compared to the non-modified pectin and also compared to the reference pectin.

EXAMPLE 3

Milk/Fruit Juice Drink

Grindsted™ URS (obtained from Danisco Ingredients, Danisco A/S) was modified with the PME as described for the yoghurt drink. The modified pectin was used in a milk/fruit juice drink which contained:

| Skimmed milk | 45.00% |
| --- | --- |
| Fruit juice | 40.00% |
| Sugar | 5.00% |
| PME modified pectin | 0.25% |
| Grindsted Flavouring | + |
| Water | 9.75% |

Dry PME modified pectin and sugar were mixed and then dissolved in water at 80° C. The pectin solution was cooled to below 5° C. and milk was added at 5° C. Grindsted Flavouring and juice were added slowly and the pH in the sample mixture was adjusted (if necessary) with citric or lactic acid to pH 4.0. The sample mixture was aged, pasteurised and homogenised as described for whey juice drink. The samples were cooled to 20° C. and filled aseptically in containers.

The results showed improved stability—including long-term stability—in the milk/fruit juice drink processed with PME modified pectin compared to the reference pectin employed in the control tests. In addition, the milk/fruit juice drink had a favourable viscosity which was lower than the control drinks. Improved functionality was also observed.

The milk/fruit juice drink can also be processed with lime and lemon pectin modified with the PME of the present invention.

EXAMPLE 4

Whey stability

The enzymatic modified pectins were tested at pH 4.0. The pH of the resultant pectin solutions were adjusted to pH 4.0 with KOH/HCl. The pectin concentration was adjusted to 1.0%. The pectins were tested in concentrations of 0.1%–0.25%. Pectin, Jenness Buffer (see below) and whey solution (see below) were mixed and heated at 96° C. for 25 min. After cooling to room temperature the absorbance is measured at 500 nm.

Dry Blend Jenness Buffer:

Dry Powder Jenness (described in Jenness, R and Koops, J *Preparation and Properties of a salt solution which simulates milk ultrafiltrate*, Nederlands Melk-en Zuiveltijd-schrift, vol 16 nr 3' pp 153–164, 1962):

15.80 g $KH_2PO_4$
5.08 g $K_3$ citrate
17.91 g $Na_3$ citrate, $2.H_2O$
1.80 g g $K_2SO_4$
13.20 g $CaCl_2$, $2.H_2O$
5.02 g $Mg_3$ citrate, $H_2O$
3.00 g $K_2CO_3$
10.78 g KCl Buffer solution:

Aqueous solution of 7.5900 g/l Dry Powder Jenness with a pH of 4.0.

Whey Solution

A concentrate of whey protein is freeze dried and pulverized. A solution of 0.40% w/w whey protein is prepared in Jenness Buffer at pH 4.0.

Pectin Solutions

1% w/w aqueous solutions of pectins are made with a pH of 4.0.

Mixture Concentrations:

Pectin, Jenness Buffer and Whey solution are mixed as indicated in the Table below. The mixtures are heated at 96° C. for 25 minutes and after cooling to room temperature the samples are measured on a spectrophotometer at 500 nm.

| μl pectin solution | μl Jenness Buffer | μl whey solution | μl total volume |
|---|---|---|---|
| 500 | 2000 | 2500 | 5000 |
| 750 | 1750 | 2500 | 5000 |
| 1000 | 1500 | 2500 | 5000 |
| 1250 | 1250 | 2500 | 5000 |

Results

The results are shown in the Table below. The quoted absorbance value at 500 nm is a mean value taken from two measurements. For comparison between the different types of pectin and the enzymatic modified pectins according to the present invention the index for non-modified pectin Grindsted™ Pectin 3450 (supplied by Danisco Ingredients, Danisco A/S) is set to 100.

An Index of >100 indicates poorer protein stability than using the sample 3450. An Index of 100 indicates similar stability to the sample 3450. An Index of <100 indicates better protein stability than using the sample 3450. An Index of 95 or <95 indicates very good protein stability.

| Pectin type | 0.10% pectin | 0.15% pectin | 0.20% pectin | 0.25% pectin |
|---|---|---|---|---|
| Grindsted™ pectin 3450 | 100 | 100 | 100 | 100 |
| Grindsted™ pectin URS | 127 | 140 | 155 | 161 |
| 5 min enz. | 100 | 108 | 115 | 113 |
| 10 min enz. | 98 | 106 | 111 | 111 |
| 15 min enz. | 92 | 94 | 100 | 100 |
| 20 min enz. | 90 | 95 | 100 | 99 |

As can be seen from the results the Grindsted™ pectin URS pectin modified according to the present invention exhibits favourable properties and in some instances very good properties for increasing stability when compared to the reference Grindsted™ pectin 3450 and the unmodified Grindsted™ pectin URS pectin.

EXAMPLE 5

Laban Drink with Long Shelf Life, Low pH

The Laban drink is an acidified milk drink with a pH value below 4.2. The laban drink consists of laban base mixed with pectin solution. The formulation for laban base is.

| | |
|---|---|
| Anhydrous milk fat | 2.8% |
| Skimmed milk powder | 10.0% |
| Grindsted flavouring | + |
| Water | 87.2% |

Standardised whole milk (anhydrous milk fat and skimmed milk powder) is homogenised at 75–80° C. and pressure of 200 bar (2900 psi) followed by pasteurisation at 90–95° C. for 5–10 min. After culturing to pH around 4.0 the pH is adjusted to 3.8–4.2 with citric or lactic acid. Pectin solution is then added. The mixture is then agitated until it is a homogeneous mixture. It is then pasteurised at 90–95° C. for 10–15 seconds and further homogenised at 150–200 bar. After cooling to 20–25° C. the product is filled aseptically in containers.

After a few days, non-stabilised laban drink often show syneresis.

However, addition of the enzymatically modified pectin according to the present invention prevents syneresis and improves the viscosity.

In addition, the product has a pronounced yoghurt taste and a long shelf life.

EXAMPLE 6

Orange Juice (Protein-Enriched)

Orange juice drink is an acidified drink (pH approx. 4) containing 2% DANPROLACT 40™ (Central Soya, Aarhus A/S), 6% sugar, 10% orange concentrate, 0.4% lemon concentrate, 0.2% pectin and 81.4% water. The product is an orange juice drink enriched with soya protein. The product is pasteurised and homogenised. After cooling to 20–25° C. the product is filled aseptically in containers and can be stored for approx. 6 months at room temperature. Addition of enzymatically modified pectins according to the present invention in orange drink (protein-enriched) showed favourable properties—such as long term stability—and it had a good mouth feel.

EXAMPLE 7

Antibody Production

Antibodies were raised against the enzyme of the present invention by injecting rabbits with the purified enzyme and isolating the immunoglobulins from antiserum according to procedures described according to N Harboe and A Ingild ("Immunization, Isolation of Immunoglobulins. Estimation of Antibody Titre" In A Manual of Quantitative Immunoelectrophoresis, Methods and Applications, N H Axelsen, et al (eds.), Universitetsforlaget, Oslo, 1973) and by T G Cooper ("The Tools of Biochemistry", John Wiley & Sons, New York, 1977).

Other modifications of the present invention will be apparent to those skilled in the art without departing from the scope of the present invention.

In the following pages a number of sequence listings are presented which have been consecutively numbered from SEQ. I.D. No. 1–SEQ. I.D. No. 19, which represent nucleotide sequences and amino acid sequences.

---

What is claimed is:

1. A process comprising:
   a) purifying a pectin methyl esterase (PME) enzyme capable of block-wise enzymatically de-esterifying pectin;
   b) adding said purified pectin methyl esterase (PME) enzyme capable of block-wise enzymatically de-esterifying pectin to a pectin;
   c) preparing a block-wise enzymatically de-esterified pectin from said pectin by said purified pectin methyl esterase (PME) enzyme capable of block-wise enzymatically de-esterifying pectin;
      i) wherein said block-wise enzymatically de-esterified pectin is a high ester pectin; and
      ii) wherein said block-wise enzymatically de-esterified pectin contains from about 70% to about 80% ester groups;
   d) adding said block-wise enzymatically de-esterified pectin to an acidic foodstuff environment comprising at least one protein; and
   e) stabilising said protein by said block-wise enzymatically de-esterified pectin.

2. A process according to claim 1 wherein the PME enzyme is a recombinant PME enzyme.

3. A process according to claim 1 wherein the foodstuff environment is an aqueous solution.

4. A process according to claim 1 wherein the protein is a dairy protein.

5. A process according to claim 4, wherein the protein is a casein or a whey protein.

6. A process according to claim 1, wherein the acidic foodstuff environment has a pH of from about 3.5 to about 5.5.

7. A process according to claim 1 wherein the acidic foodstuff environment has a pH of about 4.

8. A process according to claim 1, wherein the block-wise enzymatically de-esterified pectin is insensitive to $Ca^{2+}$ ions.

9. A process according to claim 1, wherein the block-wise enzymatically de-esterified pectin has a high-molecular weight of 50 to 150 kD.

10. A process according to claim 1, wherein the pectin methyl esterase de-esterifies two or more adjacent galacturonic acid residues of the pectin.

11. A process according to claim 1, wherein the PME enzyme is a plant PME enzyme.

12. A process according to claim 11, wherein the PME enzyme is a fruit PME enzyme.

13. A process according to claim 12, wherein the fruit is a citrus fruit.

14. A process according to claim 13, wherein the citrus fruit is an orange.

15. A process according to claim 13 wherein the PME enzyme is a lamella orange PME enzyme or an albedo orange PME enzyme.

16. A process according to claim 1 wherein the enzyme comprises an amino acid sequence selected from the group consisting of SEQ ID NO:1 and SEQ ID NO:2.

17. A process according to claim 1 wherein the PME enzyme is encoded by PME coding sequence contained in NCIMB 40749 or NCIMB 40750, or by a nucleotide sequence comprising the nucleotide sequence of SEQ ID NO:3 or SEQ ID NO:4.

18. A process according to claim 2 wherein said preparing is accomplished in the presence of sodium ions.

19. A process according to claim 1 wherein the pectin methyl esterase enzyme is immunologically reactive with an antibody raised against a second plant PME enzyme but not a tomato PME enzyme, wherein said second plant PME enzyme has the amino acid sequence of SEQ ID NO:1 or SEQ ID NO:2.

20. A process according to claim 1 wherein the foodstuff is a beverage.

21. A process according to claim 20 wherein the beverage is a drinking yoghurt, a fruit juice or a beverage comprising whey protein.

22. A process according to claim 1 wherein the block-wise enzymatically de-esterified pectin contains about 76% ester groups.

23. A process according to claim 4 wherein the protein is a milk protein.

24. A process according to claim 4 wherein the protein is a cheese protein.

25. A process according to claim 8 wherein said block-wise enzymatically de-esterified pectin has a calcium sensitivity index (CF) of 1 wherein CF is the quotient of the viscosity of a first pectin solution containing 57.6 mg calcium/g pectin divided by the viscosity of a second pectin solution containing the same concentration of pectin as said first pectin solution, said second pectin solution not containing calcium.

26. A process according to claim 6, wherein the pH is in the range of from 4 to about 5.5.

27. A process comprising:
   a) obtaining a pectin methyl esterase (PME) enzyme capable of block-wise enzymatically de-esterifying pectin;
   b) contacting said PME enzyme and a pectin to produce a block-wise enzymatically de-esterified pectin;
      i) wherein said block-wise enzymatically de-esterified pectin is a high ester pectin; and
      ii) wherein said block-wise enzymatically de-esterified pectin contains from about 70% to about 80% ester groups;
   c) adding said block-wise enzymatically de-esterified pectin to an acidic foodstuff environment comprising at least one protein such that said protein is stabilized by said block-wise enzymatically de-esterified pectin.

* * * * *